United States Patent
Josse et al.

(10) Patent No.: US 11,286,507 B2
(45) Date of Patent: Mar. 29, 2022

(54) ANAEROBIC DIGESTION AND PYROLYSIS SYSTEM

(71) Applicant: ANAERGIA INC., Burlington (CA)

(72) Inventors: Juan Carlos Josse, Mission Viejo, CA (US); Andrew Benedek, Rancho Santa Fe, CA (US); Michael David Theodoulou, Milton (CA)

(73) Assignee: ANAERGIA INC., Burlington (CA)

( * ) Notice: Subject to any disclaimer, the term of this patent is extended or adjusted under 35 U.S.C. 154(b) by 0 days.

(21) Appl. No.: 14/903,904

(22) PCT Filed: Jul. 11, 2014

(86) PCT No.: PCT/CA2014/050662
§ 371 (c)(1),
(2) Date: Jan. 8, 2016

(87) PCT Pub. No.: WO2015/003273
PCT Pub. Date: Jan. 15, 2015

(65) Prior Publication Data
US 2016/0153008 A1    Jun. 2, 2016

Related U.S. Application Data

(60) Provisional application No. 61/846,863, filed on Jul. 16, 2013, provisional application No. 61/845,054, filed on Jul. 11, 2013.

(51) Int. Cl.
*C12P 5/02*     (2006.01)
*C10B 53/02*    (2006.01)
(Continued)

(52) U.S. Cl.
CPC .............. *C12P 5/023* (2013.01); *C02F 11/04* (2013.01); *C02F 11/10* (2013.01); *C10B 53/02* (2013.01);
(Continued)

(58) Field of Classification Search
CPC ........... C12P 5/023; C02F 11/10; C02F 11/04; C10B 47/44; C10B 5/02; C10K 1/04;
(Continued)

(56) References Cited

U.S. PATENT DOCUMENTS 4,153,514 A    5/1979  Garrett et al.
4,289,625 A *  9/1981  Tarman ...................... C10J 3/20
                                                  210/603
(Continued)

FOREIGN PATENT DOCUMENTS

BR    9401102 A    11/1994
CA    2628323 A1    6/2007
(Continued)

OTHER PUBLICATIONS

ASTM, Section D3172, Proximate Analsys of Coal and Coke, (2007).
(Continued)

*Primary Examiner* — Latosha Hines
(74) *Attorney, Agent, or Firm* — Borden Ladner Gervais; Michael J. Damiani

(57) ABSTRACT

An anaerobic digester is fed a feedstock, for example sludge from a municipal wastewater treatment plant, and produces a digestate. The digestate is dewatered into a cake. The cake may be dried further, for example in a thermal drier. The cake is treated in a pyrolysis system to produce a synthesis gas and biochar. The gas is sent to the same or another digester to increase its methane production. The char may be used as a soil enhancer.

16 Claims, 14 Drawing Sheets

(51) Int. Cl.
*C02F 11/04* (2006.01)
*C02F 11/10* (2006.01)
*C10K 1/06* (2006.01)
*C12M 1/107* (2006.01)
*C12M 1/00* (2006.01)
*C10K 1/04* (2006.01)
*C10B 47/44* (2006.01)

(52) U.S. Cl.
CPC .............. *C10K 1/06* (2013.01); *C12M 21/04* (2013.01); *C12M 45/20* (2013.01); *C10B 47/44* (2013.01); *C10K 1/04* (2013.01); *Y02E 50/10* (2013.01); *Y02E 50/30* (2013.01); *Y02P 20/145* (2015.11); *Y02W 10/20* (2015.05); *Y02W 10/40* (2015.05)

(58) Field of Classification Search
CPC ......... C10K 1/06; C12M 21/04; C12M 45/20; Y02E 50/14; Y02E 50/343; Y02W 10/23; Y02W 10/40
USPC ........................................... 435/167
See application file for complete search history.

(56) References Cited

U.S. PATENT DOCUMENTS

| | | | |
|---|---|---|---|
| 4,522,151 | A | 6/1985 | Arbisi et al. |
| 4,759,300 | A | 7/1988 | Hansen et al. |
| 4,880,473 | A | 11/1989 | Scott et al. |
| 4,935,038 | A | 6/1990 | Wolf |
| 5,017,196 | A | 5/1991 | Dewitz |
| 5,395,455 | A | 3/1995 | Scott et al. |
| 5,417,492 | A | 5/1995 | Christian et al. |
| 5,424,417 | A | 6/1995 | Torget et al. |
| 5,605,551 | A | 2/1997 | Scott et al. |
| 5,865,898 | A | 2/1999 | Holtzapple et al. |
| 5,959,167 | A | 9/1999 | Shabtai et al. |
| 6,022,419 | A | 2/2000 | Torget et al. |
| 6,048,374 | A | 4/2000 | Green |
| 6,228,177 | B1 | 5/2001 | Torget |
| 7,229,483 | B2 | 6/2007 | Lewis |
| 7,494,637 | B2 | 2/2009 | Peters et al. |
| 7,578,927 | B2 | 8/2009 | Marker et al. |
| 7,608,439 | B2 | 10/2009 | Offerman et al. |
| 7,972,824 | B2 | 7/2011 | Simpson et al. |
| 8,119,076 | B2 | 2/2012 | Keusenkothen et al. |
| 8,383,871 | B1 | 2/2013 | Sellars et al. |
| 8,632,024 | B2 * | 1/2014 | Gitschel ............... C10L 3/106 |
| | | | 241/19 |
| 8,777,468 | B2 | 7/2014 | Suehiro et al. |
| 8,877,468 | B2 | 11/2014 | Lewis |
| 8,993,288 | B2 | 3/2015 | Lewis |
| 9,534,174 | B2 * | 1/2017 | Mazanec ............... C10K 1/04 |
| 2003/0071372 | A1 | 4/2003 | Scherzinger et al. |
| 2004/0084366 | A1 | 5/2004 | Anderson et al. |
| 2006/0112639 | A1 | 6/2006 | Nick et al. |
| 2006/0289356 | A1 | 12/2006 | Burnett et al. |
| 2007/0117195 | A1 | 5/2007 | Warner et al. |
| 2007/0217995 | A1 | 9/2007 | Matsumura et al. |
| 2008/0035561 | A1 | 2/2008 | Gray (Gabb) et al. |
| 2008/0236042 | A1 | 10/2008 | Summerlin |
| 2008/0280338 | A1 | 11/2008 | Hall et al. |
| 2008/0317657 | A1 | 12/2008 | Hall et al. |
| 2009/0151253 | A1 | 6/2009 | Manzer et al. |
| 2009/0229595 | A1 | 9/2009 | Schwartz, Jr. |
| 2009/0239279 | A1 * | 9/2009 | Hall .................... C12P 5/02 |
| | | | 435/167 |
| 2010/0021979 | A1 | 1/2010 | Facey et al. |
| 2010/0133085 | A1 | 6/2010 | Hutchins et al. |
| 2010/0162627 | A1 | 7/2010 | Clomburg, Jr. et al. |
| 2010/0223839 | A1 | 9/2010 | Garcia-Perez et al. |
| 2010/0317070 | A1 | 12/2010 | Agaskar |
| 2011/0033908 | A1 | 2/2011 | Cheong et al. |
| 2011/0179700 | A1 | 7/2011 | Monroe et al. |
| 2011/0248218 | A1 | 10/2011 | Sutradhar et al. |
| 2011/0278149 | A1 | 11/2011 | Hornung et al. |
| 2012/0073199 | A1 * | 3/2012 | Lewis ................... C10B 53/02 |
| | | | 48/127.5 |
| 2012/0322130 | A1 | 12/2012 | Garcia-Perez et al. |
| 2013/0134089 | A1 | 5/2013 | Cote |
| 2013/0203144 | A1 | 8/2013 | Josse et al. |
| 2013/0316428 | A1 | 11/2013 | Gonella |
| 2014/0183022 | A1 | 7/2014 | Daugaard et al. |
| 2016/0024390 | A1 | 1/2016 | Ullom |
| 2017/0240814 | A1 | 8/2017 | Dalluge et al. |
| 2019/0091739 | A1 | 3/2019 | Benedek et al. |

FOREIGN PATENT DOCUMENTS

| | | | | |
|---|---|---|---|---|
| CA | 2641270 | A1 | 12/2009 | |
| CN | 104609698 | A | 5/2015 | |
| DE | 10107712 | A1 | 9/2002 | |
| EP | 0359250 | A2 | 3/1990 | |
| EP | 0521685 | A2 | 1/1993 | |
| EP | 1207040 | A2 | 5/2002 | |
| EP | 1568478 | A1 | 8/2005 | |
| GB | 1571886 | A | 7/1980 | |
| GB | 2257137 | A | 1/1993 | |
| GB | 2332196 | A | 6/1999 | |
| JP | 2003089793 | A | 3/2003 | |
| WO | 0179123 | A1 | 10/2001 | |
| WO | 2004060587 | A1 | 7/2004 | |
| WO | 2006056620 | A1 | 6/2006 | |
| WO | 2010001137 | A2 | 1/2010 | |
| WO | 2011128513 | A1 | 10/2011 | |
| WO | 2012166771 | A2 | 12/2012 | |
| WO | WO 2012166771 | A2 * | 12/2012 | ............. C02F 11/04 |
| WO | WO-2012166771 | A2 * | 12/2012 | ............. C02F 11/04 |
| WO | 2013110186 | A1 | 8/2013 | |
| WO | 2015050433 | A1 | 4/2015 | |
| WO | 2015053617 | A1 | 4/2015 | |
| WO | 2017161445 | A1 | 9/2017 | |

OTHER PUBLICATIONS

AWWTA, Standard Methods, Section 240G, (2000).
Bredwell et al., "Reactor Design Issues for Synthesis-Gas Fermentations, Biotechnology Process," Biotechnology Process, 1999, vol. 15 (5), pp. 834-844.
Cozzani et al., "A Fundamental Study on Conventional Pyrolysis of a Refuse-Derived Fuel," Industrial & Engineering Chemistry Research, 1995, 34, 2006-2020.
Demirbas et al., "Biomass Resource Facilities and Biomass Conversion Processing for Fuels and Chemicals," Energy Conversion and Management, Jul. 2001, vol. 42 (11), pp. 1357-1378.
Demirbas et al., "The Influence of Temperature on the Yields of Compounds Existing in Bio-Oils Obtained from Biomass Samples via Pyrolysis," Fuel Processing Technology, Jun. 2007, vol. 88 (6), pp. 591-597.
European Patent Application No. 13740592, Supplementary European Search Report dated Jul. 27, 2015.
European Patent Application No. 16162806, Extended European Search Report dated Dec. 14, 2016.
Excerpts from Traite De Polarimetrie, Georges Bruhat, Paris, France, 1930.
Garcia-Perez, "Challenges and Opportunities of Biomass Pyrolysis to Produce Second Generation Bio-fuels and Chemicals," Auburn University, Jun. 13, 2012, 66 pages.
Guiot et al., "Potential of Wastewater-Treating Anaerobic Granules for Biomethanation of Synthesis Gas," Environmental Science and Technology, Mar. 2011, vol. 45 (5), pp. 2006-2012.
Gullu et al., "Biomass to Methanol via Pyrolysis Process," Energy Conversion and Management, Jul. 2001, vol. 42 (11), pp. 1349-1356.
International Patent Application No. PCT/CA2013/050037, International Preliminary Report on Patentability dated Aug. 7, 2014.
International Patent Application No. PCT/CA2013/050037, International Search Report dated Apr. 4, 2013.

(56) References Cited

OTHER PUBLICATIONS

International Patent Application No. PCT/CA2014/050662, International Preliminary Report on Patentability dated Jan. 12, 2016.
International Patent Application No. PCT/CA2014/050662, International Search Report and Written Opinion dated Sep. 25, 2014.
Jenkins, "Oxidation-Based Water-Reuse Technology that Improves Mass Transfer," Chemical Engineering, Feb. 2013, p. 12.
Jones, et al., "Production of Gasoline and Diesel from biomass via Fast Pyrolysis" Hydrotreating and Hydrocracking: A Design Case, U.S. Department of Energy, PNNL-18284 Feb. 28, 2009, 76 pages.
Laemsak, "Wood Vinegar Presentation," Undated, 5 pages.
Laird et al., "Sustainable Alternative Fuel Feedstock Opportunities, Challenges and Roadmaps for Six U.S. Regions," Chapter 16: Pyrolysis and Biochar—Opportunities for Distributed Production and Soil Quality Enhancement, Proceedings of the Sustainable Feedstocks for Advance Biofuels Workshop, Atlanta, GA, Sep. 28-30, 2010, pp. 257-281.
Lehmann et al., "Bio-Char Sequestration in Terrestrial Ecosystems—A Review," Mitigation and Adaptation Strategies for Global Change, Mar. 2006, vol. 11 (2), pp. 403-427.
Lewis et al., "A Powerful by Product," WEFTEC, Jan. 2008, pp. 64-69.
Lian et al., "Separation, Hydrolysis and Fermentation of Pyrolytic Sugars to Produce Ethanol and Lipids," Bioresource Technology, Dec. 2010, vol. 101 (24), pp. 9688-9699.
Liaw et al., "Effect of Pyrolysis Temperature on the Yield and Properties of Bio-oils Obtained From the Auger Pyrolysis of Douglas Fir Wood," Journal of Analytical and Applied Pyrolysis, Jan. 2012, vol. 93, pp. 52-62.
Linden et al., "Gaseous Product Distribution in Hydrocarbon Pyrolysis," Industrial and Engineering Chemistry, 1955, vol. 47 (12), pp. 2470-2474.
Mahulkar et al., "Steam Bubble Cativation," AIChE Journal, Jul. 2008, vol. 54 (7), pp. 1711-1724.
Melin et al., "Evaluation of Lignocellulosic Biomass Upgrading Routes to Fuels and Chemicals," Cellulose Chemistry and Technology, 2010, vol. 44 (4-6), pp. 117-137.
Parry, Biosolids Technology Advances, Jan. 2012, 20 Pages.
Parry, et al. "Prolysis of Dried Biosolids for Increased Biogas Production" Proceedings of the Water Environment Federation, Residuals and Biosolids, Mar. 2012, pp. 1128-1139.
Shanley Pump and Equipment, Inc., EDUR Pumps, [online], printed May 30, 2014. Retrieved from the Internet:.
Smith et al., "Integrating Pyrolysis and Anaerobic Digestion," The Northwest Bio-energy Symposium, Seattle, Washington, Nov. 13, 2012, 44 pages, http://www.pacificbiomass.org/documents/Smith.pdf.
Sustarsic, "Wastewater Treatment: Understanding the Activated Sludge Process" CEP Nov. 2009, pp. 26-29.
U.S. Appl. No. 13/826,507, Advisory Action dated May 22, 2015.
U.S. Appl. No. 13/826,507, Notice of Allowance dated Sep. 29, 2016.
U.S. Appl. No. 13/826,507, Office Action dated Feb. 26, 2016.
U.S. Appl. No. 13/826,507, Office Action dated Jul. 7, 2014.
U.S. Appl. No. 13/826,507, Office Action dated Mar. 18, 2015.
U.S. Appl. No. 13/826,507, Restriction Requirement dated Apr. 11, 2014.
U.S. Appl. No. 14/373,714, Notice of Allowance dated Feb. 10, 2016.
U.S. Appl. No. 14/373,714, Office Action dated Jul. 24, 2015.
Vit et al., English language abstract of DE10107712, published Sep. 5, 2002.
Written Opinion for Application No. PCT/CA2013/050037, dated Apr. 4, 2013, 7 pages.
Yang et al., "Pretreatment: The Key to Unlocking Low-Cost Cellulosic Ethanol," Biofuels, Bioproducts and Biorefinering, Jan. 2008, vol. 2 (1), pp. 26-40.
Zhang et al., "Influence of Manure Types and Pyrolysis Conditions on the Oxidation Behavior of Manure Char," Bioresource Technology, Sep. 2009, vol. 100 (18), pp. 4278-4283.

International Patent Application No. PCT/CA2016/050103, International Search Report and Written Opinion dated May 26, 2016.
Water and Sewage Treatment Energy Management Joint Conference, Delaware Valley Regional Planning Commission, Apr. 25, 2012, 55 Pages.
Zanzi et al., "Rapid Pyrolysis of Agricultural Residues at High Temperature," Biomass and Bioenergy, Nov. 2002, vol. 23 (5), 4 pages.
U.S. Appl. No. 13/136,180, Notice of Allowance dated Jul. 8, 2014.
U.S. Appl. No. 13/136,180, Notice of Allowance dated Mar. 4, 2014.
U.S. Appl. No. 13/136,180, Office Action dated Mar. 20, 2013.
U.S. Appl. No. 13/136,180, Office Action dated Nov. 2, 2012.
U.S. Appl. No. 14/031,758, Notice of Allowance dated Nov. 28, 2014.
U.S. Appl. No. 14/031,758, Office Action dated Apr. 28, 2014.
U.S. Appl. No. 14/631,144, Notice of Allowance dated Apr. 15, 2016.
U.S. Appl. No. 14/631,144, Office Action dated Nov. 12, 2015.
U.S. Appl. No. 15/015,479, Notice of Allowance dated Sep. 8, 2017.
U.S. Appl. No. 15/015,479, Office Action dated Feb. 24, 2017.
U.S. Appl. No. 15/085,381, Notice of Allowance dated Sep. 21, 2017.
U.S. Appl. No. 15/085,381, Office Action dated Apr. 19, 2017.
Bridgewater., et al., "An Overview of Fast Pyrolysis of Biomass", Organic Geochemistry, Dec. 1999, vol. 30 (12), pp. 1479-1493. Retrieved from the Internet:[https://www.researchgate.net/profile/Dietrich_Meier/publication/222485410_An_Overview_of_Fast_pyrolysis_of_Biomass/links/02bfe512926de56965000000.pdf].
Canadian Patent Application No. 2,862,132, Office Action dated Mar. 5, 2019.
Chen et al., "Pyrolysis Technologies for Municipal Solid Waste: A Review," Waste management, Dec. 2014, vol. 34 (12), pp. 2466-2486.
Chinese Patent Application No. 201610542016.4, Office Action dated Jun. 23, 2020—English Translation Available.
Chinese Patent Application No. 201610542016.4, Office Action dated Jan. 13, 2021—English Translation Not Available.
Corporate Literature., "Pacific Pyrolysis—Technology", Pacific Pyrolysis Corp., Jun. 2017, 4 pages. Retrieved from the Internet: [http://pacificpyrolysis.com/technology.html].
European Patent Application No. 13740592.4, Office Action dated Aug. 23, 2018.
European Patent Application No. 17765614.7, Extended European Search Report dated Nov. 8, 2019.
European Patent Application No. 17769208.4, Extended European Search Report dated Oct. 18, 2019.
European Patent Application No. 13740592.4, Communication pursuant to Article 94(3) EPC dated Jan. 17, 2018.
Fabbri et al., "Linking Pyrolysis and Anaerobic Digestion (Py-AD) for the Conversion of Lignocellulosic Biomass," Current Opinion in Biotechnology, Apr. 2016, vol. 38, pp. 167-173. XP029496680.
Gomes et al., "Methodology for Burner Design-Combustion of Pyrolysis Gas from Charcoal Production," 24th ABCM International Congress of Mechanical Engineering, Dec. 3-8, 2017, 7 pages.
Huang et al., "Intelligent Solid Waste Processing Using Optical Sensor Based Sorting Technology," 2010 3rd International Congress on Image and Signal Processing, Nov. 2010, pp. 1657-1661.
International Patent Application No. PCT/CA2016/050103, International Preliminary Report on Patentability dated Aug. 17, 2017.
International Application No. PCT/CA2017/050335, International Preliminary Report on Patentability dated Oct. 4, 2018.
International Application No. PCT/CA2017/050336, International Preliminary Report on Patentability dated Sep. 27, 2018.
International Application No. PCT/CA2019/051240, International Preliminary Report on Patentability dated Mar. 18, 2021.
International Patent Application No. PCT/CA2017/050335, International Search Report and Written Opinion dated Jun. 22, 2017.
International Patent Application No. PCT/CA2017/050336, International Preliminary Report on Patentability dated Sep. 18, 2018.
International Patent Application No. PCT/CA2017/050336, International Search Report and Written Opinion dated Jun. 22, 2017.

(56) References Cited

OTHER PUBLICATIONS

International Patent Application No. PCT/CA2019/051240, International Search Report and Written Opinion dated Nov. 14, 2019.
McKendry., "Energy Production from Biomass (Part 3): Gasification Technologies," Bioresource Technology, May 2002, vol. 83 (1), pp. 55-63. Retrieved from the Internet: [https://eclass.duth.gr/modules/document/file.php/].
Singapore Patent Application No. SG10201908192U, Written Opinion dated Sep. 17, 2020.
U.S. Appl. No. 15/389,901, Restriction Requirement dated Feb. 26, 2019.
U.S. Appl. No. 16/124,763, Non-Final Office Action dated Sep. 25, 2019.
U.S. Appl. No. 16/083,000, Non-Final Office Action dated Dec. 12, 2019.
U.S. Appl. No. 16/124,763, Non-Final Office Action dated Feb. 11, 2021.
U.S. Appl. No. 16/083,000, Final Office Action dated Jun. 18, 2020.
U.S. Appl. No. 16/124,763, Non-Final Office Action dated May 4, 2020.
U.S. Appl. No. 15/389,901, Non-Final Office Action dated Jul. 22, 2019.
U.S. Appl. No. 16/083,000, Advisory Action dated Sep. 11, 2020.
U.S. Appl. No. 16/124,763, Final Office Action dated Jan. 17, 2020.
U.S. Appl. No. 16/124,763, Final Office Action dated Sep. 14, 2020.
U.S. Appl. No. 16/083,000, Non-Final Office Action dated Nov. 20, 2020.
U.S. Appl. No. 16/124,763, Advisory Action dated Nov. 23, 2020.
U.S. Appl. No. 15/705,704, Restriction Requirement dated Feb. 28, 2020.
Woolf et al., "An Open-Source Biomass Pyrolysis Reactor," Biofuels, Bioproducts, and Biorefining, Sep. 2017, vol. 11 (6), pp. 945-954.
Chinese Patent Application No. 201610542016.4, Office Action dated Apr. 26, 2021—English Translation Available.
U.S. Appl. No. 16/083,000, Notice of Allowance dated Jun. 21, 2021.
U.S. Appl. No. 16/083,000, Notice of Allowance dated May 21, 2021.

* cited by examiner

PBM Bio-oil Batch Digestion Test

| Digester | F/M (g COD/g COD) | Total COD load (g) | COD load ratio (g oil COD/g sludge COD) | Theoretical biogas production (ml) |
|---|---|---|---|---|
| A (control) | 0.18 | 1.05 | 0 | 326 |
| B | 0.17 | 1.04 | 0.23 | 322 |
| C | 0.21 | 1.23 | 0.45 | 381 |
| D | 0.27 | 1.62 | 0.91 | 502 |

Main assumptions used for theoretical biogas production:
1) 0.35 L stp $CH_4$/g COD destroyed;
2) COD conversion ratio of 50%;
3) Biogas composition: 65 v/v% $CH_4$ and 35 v/v% $CO_2$;
4) 1 L biogas at 0°C and 1 atm. = 1.14 L biogas at 37°C and 1 atm.

FIG. 10

ANAEROBIC DIGESTION AND PYROLYSIS SYSTEM

CROSS-REFERENCE TO RELATED APPLICATIONS

This application is a National Stage Entry of International Application No. PCT/CA2014/050662, filed Jul. 11, 2014, which is a non-provisional application of U.S. Application Ser. No. 61/845,054, filed Jul. 11, 2013 and U.S. Application Ser. No. 61/846,863 filed Jul. 16, 2013. International Application No. PCT/CA2014/050662 and U.S. Application Serial Nos. 61/845,054 and 61/846,863 are incorporated by reference.

FIELD

This specification relates to wastewater treatment, anaerobic digestion, waste-to-energy processes and pyrolysis.

BACKGROUND

The following discussion is not an admission that anything discussed below is common general knowledge or citable as prior art.

Anaerobic digestion produces biogas as a result of the biological fermentation of volatile solids (VS) supplied with the feedstock. The degree of volatile solids reduction is related to the biodegradability of the feedstock and process conditions in the digester. Important digester parameters or considerations include temperature, pH, food-to-microorganism ratio, organic loading rate, hydraulic and solids retention time, absence of toxic substances at inhibitory concentrations, adequate mixing, and others. The closer these conditions are to an optimum, the higher the VS reduction will be.

Typically, digesters treating complex organic substrates will achieve 60 to 80% VS reduction. With substrates with high fiber content, such as silage or dairy manure, a digester may achieve about 60% VS destruction. Typical digesters treating municipal sewage sludge produced in a wastewater treatment plant usually achieve about 50% VS destruction in 20 day hydraulic retention time (HRT) mesophilic digesters.

The digester sludge, or digestate, produced by an anaerobic digester is a combination of inert solids that were fed with the substrate, recalcitrant volatile solids that could not be degraded biologically, and bacterial biomass that grew as a result of feeding on the degradable portion of the volatile solids fed with the feedstock. A typical digestate solids content is 2% to 10% total solids (TS) or dried solids (DS), depending on the substrate and the type of digester. The digestate may be dewatered mechanically to produce a cake with 20 to 30% solids, depending among other things on the undigested fiber content and the type of dewatering device used.

Pyrolysis is a thermo-chemical process typically used to process solid waste such as wood chips or sawdust. Pyrolysis produces biochar, liquids and gases from a biomass by heating the biomass in a low or no oxygen environment. The absence or deficiency of oxygen prevents combustion. The relative yield of products from pyrolysis varies with temperature. Temperatures of 400-500° C. (752-932° F.) produce more char, while higher temperatures, up to and above 700° C. (1,292° F.) favor the yield of liquid and gaseous fuel components. Pyrolysis occurs more quickly at the higher temperatures, typically requiring seconds instead of hours. High temperature pyrolysis is also known as gasification, and produces primarily synthesis gas. Low temperature pyrolysis is also known as torrefaction and produces relatively more char. Once initiated, both processes can be self-supporting under some conditions and produce net energy, not accounting for the energy value of the biomass consumed.

INTRODUCTION TO THE INVENTION

The following introduction is intended to introduce the reader to the detailed description and claims to follow, but is not intended to limit or define the claims.

The solids in digestate and other biosolids have an energy content resulting from their potential to be oxidized. This energy content can be extracted by pyrolysis of biosolids to produce gaseous or liquid (including vapor) products. In this specification, the word syngas or pyrolysis gas may be used to refer to a combination of gaseous and liquid (or vapor) products unless the context indicates that a specific product type is intended. One or more of the biosolid pyrolysis products can be converted to a biogas containing mostly methane by anaerobic microorganisms, in particular methanogens. Further, other waste materials may be pyrolyzed. These other waste materials include, for example, waste from food processing, agriculture or forestry, municipal solid waste, refuse derived fuel, and green waste (i.e. grass clippings, plant trimmings etc. from homes, parks or other properties). These other waste materials typically include biomass but may also include non-bio-based organic materials such as plastics. One or more products of pyrolysing any of these other waste materials can also be converted to a biogas containing mostly methane by anaerobic microorganisms, in particular methanogens.

A large wastewater treatment system, for example a municipal sewage plant, often has an anaerobic digester. The anaerobic digester receives primary or secondary sludge, or both, from an activated sludge or other process. The digester further decomposes the sludge, thus reducing the volume of sludge to be disposed of. The digester also produces biogas. In theory, the biogas is usable as a fuel. In practice, however, the cost of biogas upgrading equipment necessary to sell the biogas to a natural gas utility or burn the gas to generate electricity on site prohibits the recovery of biogas as a fuel from all but the largest municipal sewage plants. The vast majority of biogas is flared or otherwise wasted.

In a system and process to be described in the detailed description, one or more of biosolids and another waste material (for example any one or more of the other waste materials mentioned above in this introduction) are pyrolyzed. One or more products of this pyrolysis are feed into an anaerobic digester. In this way, the biogas production of the digester is increased. In addition, a means is provided for reducing the volume of biosolids or other waste that needs to be treated or disposed of.

In one example, a municipal sewage treatment plant or industrial wastewater treatment plant includes an anaerobic digester treating sludge from a wastewater treatment process. A pyrolyser receives digestate from the digester. Optionally, the same or another pyrolyser receives sludge from the wastewater treatment process or another waste such as municipal solid waste, refuse derived fuel or green waste. One or more products produced by the one or more pyrolysers is sent to the digester. In some cases, the increase in biogas production may make it practical to upgrade the biogas for combustion to generate electricity on site or injection into a natural gas pipeline.

In a process and apparatus described herein, syngas is added into an anaerobic digester to produce methane. The syngas can come from pyrolysis or gasification of a raw biomass such as wood, municipal solids waste, municipal yard waste, waste activated sludge from municipal sewage treatment, agricultural residues, etc., or from pyrolysis or gasification of a dewatered and optionally partially dried digestate cake produced by the same or another digester at the same or another digestion facility. For example, the digester may be part of a municipal wastewater treatment plant or an agricultural or industrial digester. Methane production in the digester increases. The syngas may be added to the digester without pretreatment other than lowering its temperature.

An apparatus and process are described herein for transferring syngas to digestate. A jet ejector pump is used to aspirate into a stream of digestate flowing in a pipe. The digestate may be flowing in a dedicated recirculation loop. A pump generates a primary flow. An ejector nozzle at the pump discharge draws and mixes a secondary flow of syngas into the primary flow. The liquid and gas are combined into a liquid jet containing fine syngas bubbles. This mixture exits in one or more locations in a digester tank.

Optionally, the pumped jet aspiration system may also provide mixing for the digester. In another option, gas from the headspace of the digester can be mixed into digestate to encourage further conversion of CO and $H_2$ in the syngas or biogas to methane. In another option, heat from syngas leaving a pyrolysis reactor may be recovered and used, for example, for partial drying of the digestate.

Optionally, a condensable portion of the syngas may be condensed, for example by indirect condensing, and fed to the digester as a liquid. A remaining gas portion of the syngas is fed to the digester as described above.

In a process and apparatus for treating wastewater, such as municipal sewage, a digestate cake is further thermally dried and then fed to a pyrolysis system to produce syngas and char. The syngas is preferably cooled to recover its heat for cake drying, and then introduced into one or more anaerobic digesters for bioconversion of syngas into methane. The methane may be used as a fuel for heat or generating electricity. The biochar resulting from the pyrolysis process may be used as soil enhancer.

BRIEF DESCRIPTION OF THE FIGURES

FIGS. 8 to 12 are graphs of experimental results.

DETAILED DESCRIPTION

Figure 1:
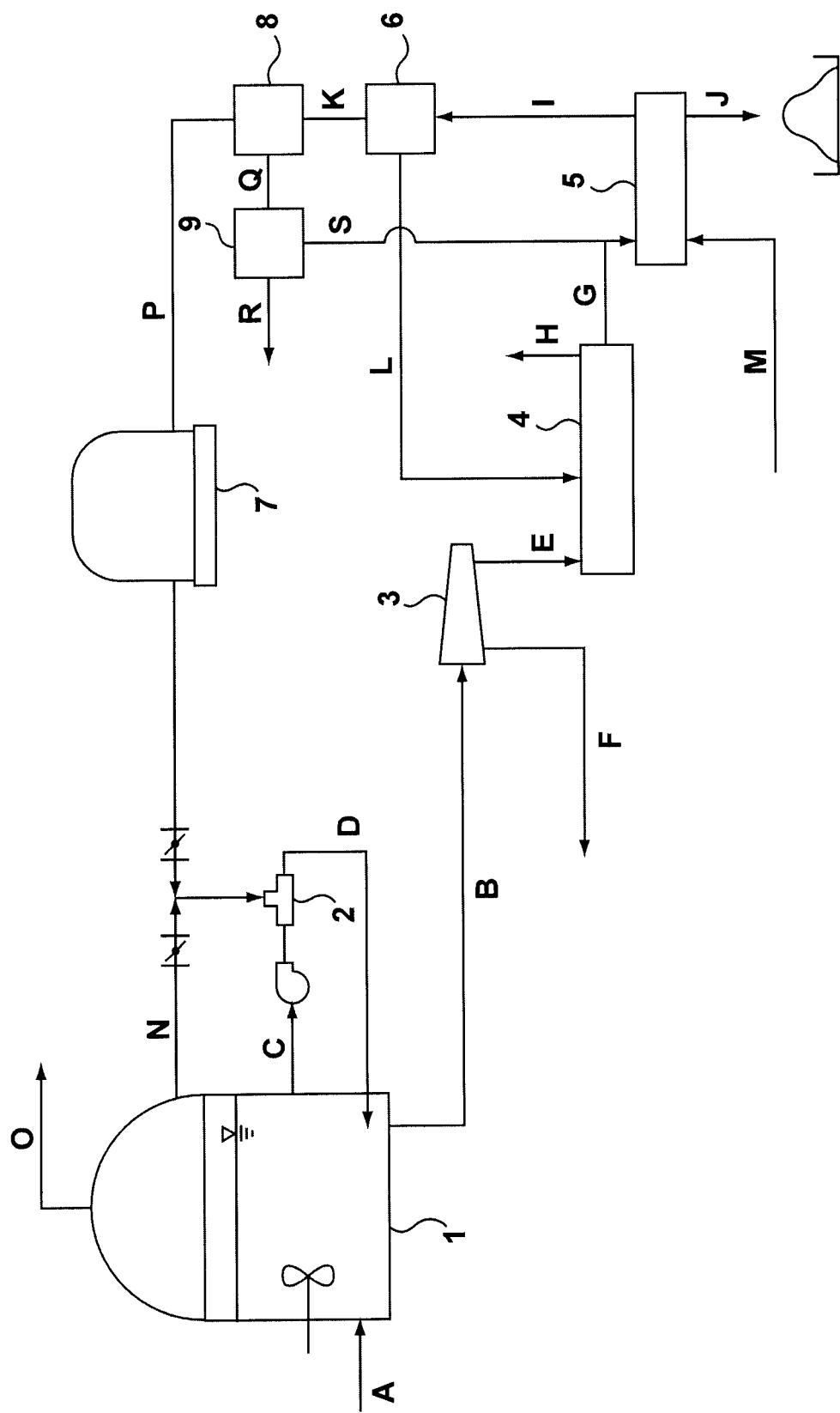
FIG. 1 is a schematic process flow diagram of an anaerobic digestion and pyrolysis system.
Figure 2:
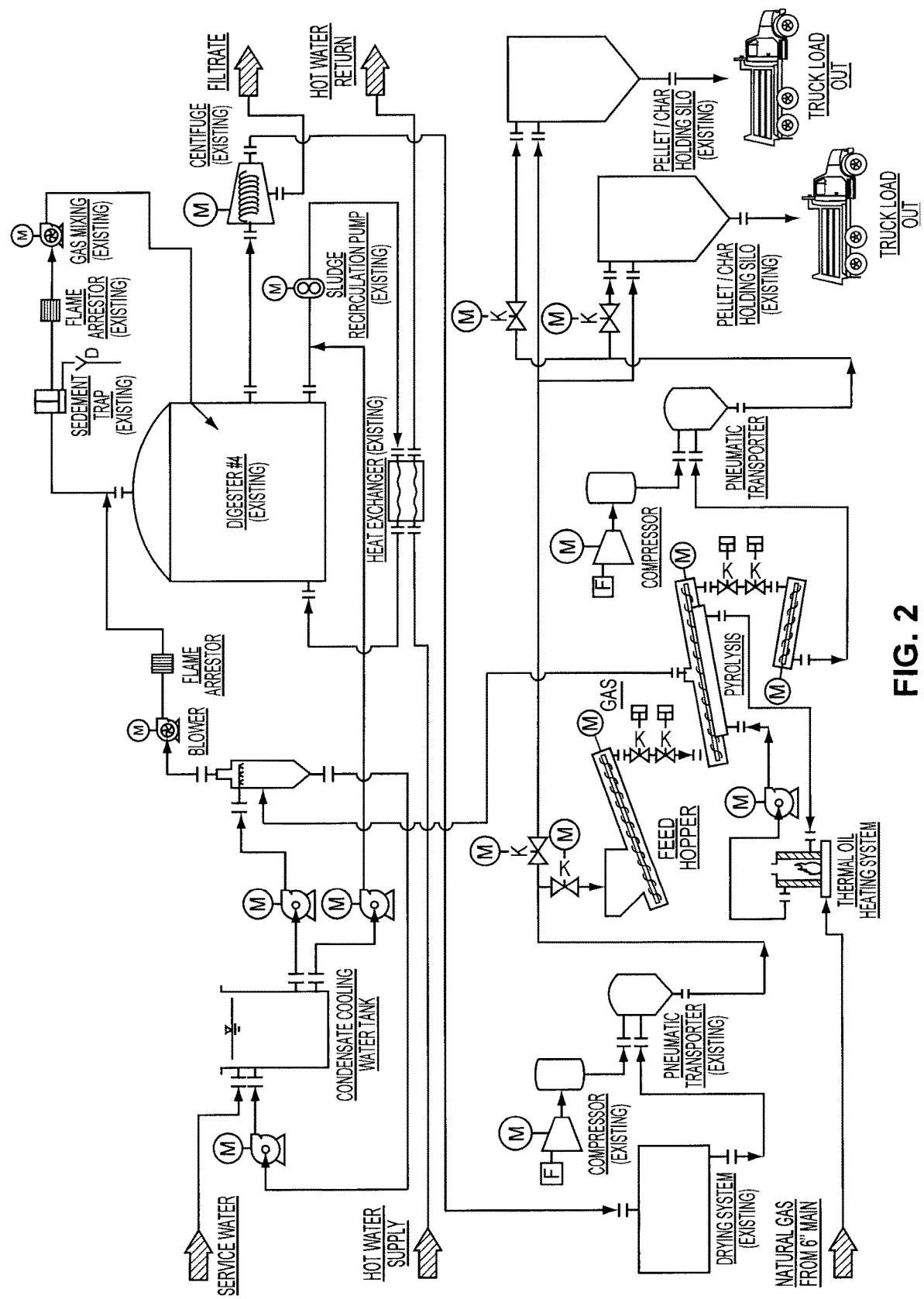
FIGS. 2 to 7 are a set of process flow diagrams and/or process and instrumentation diagrams for a design example.
Figure 3:
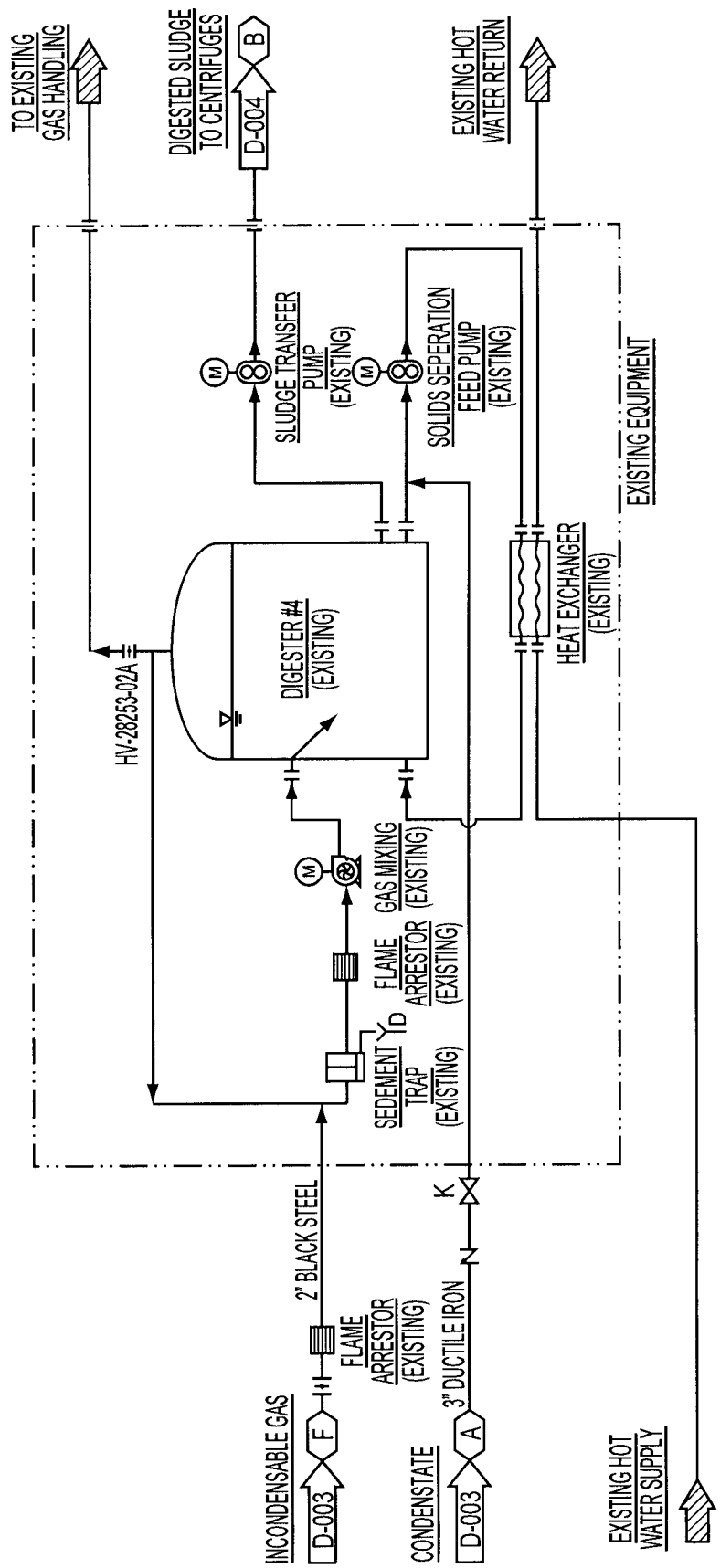
Figure 4:
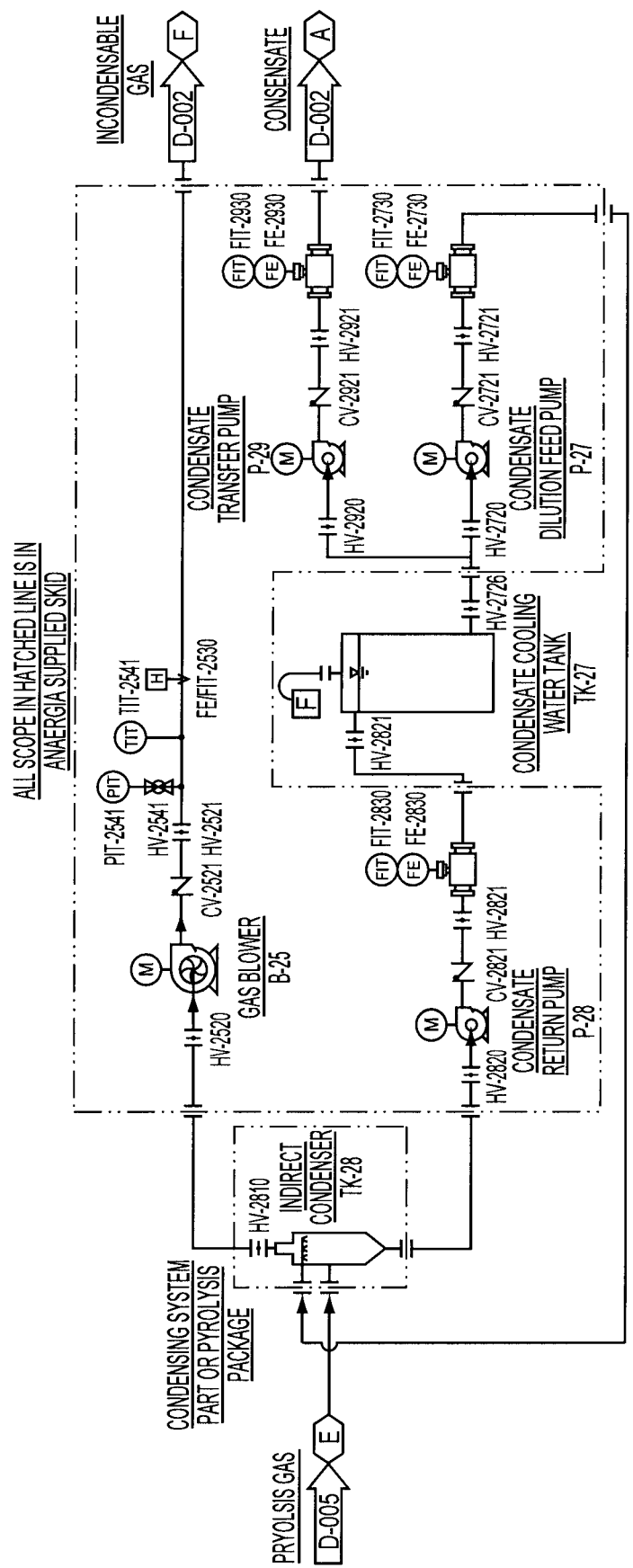
Figure 5:
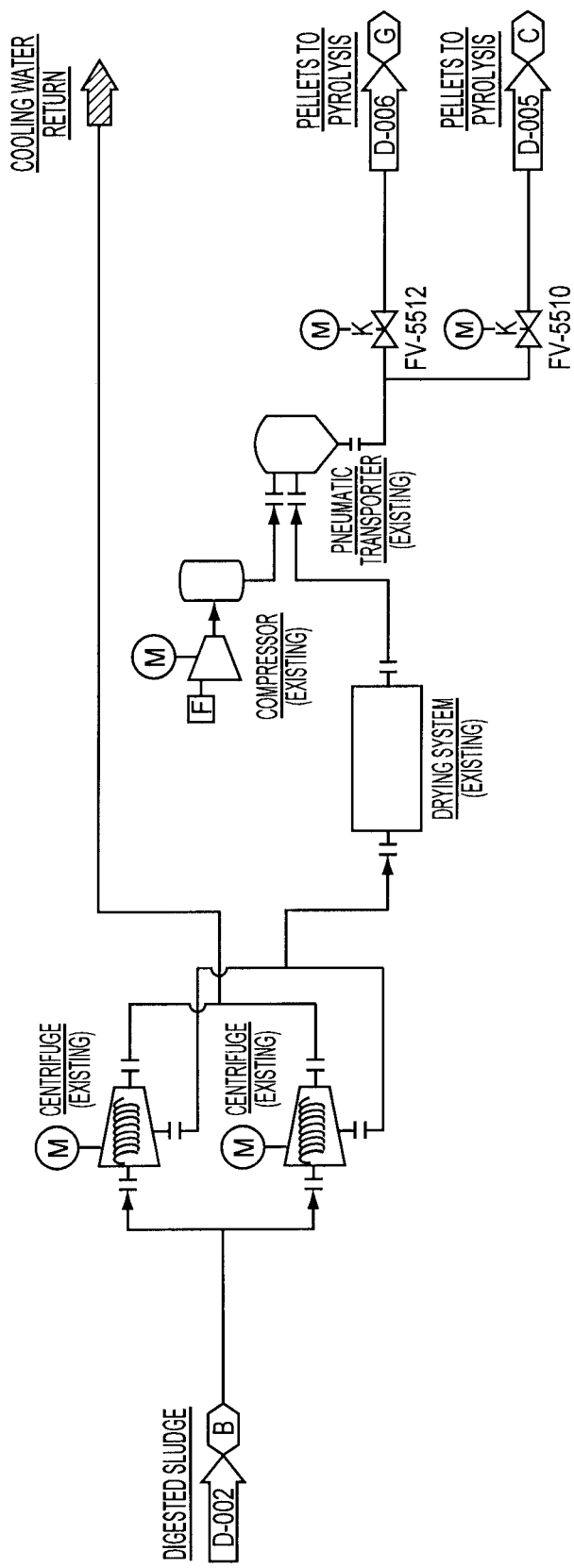
Figure 6:
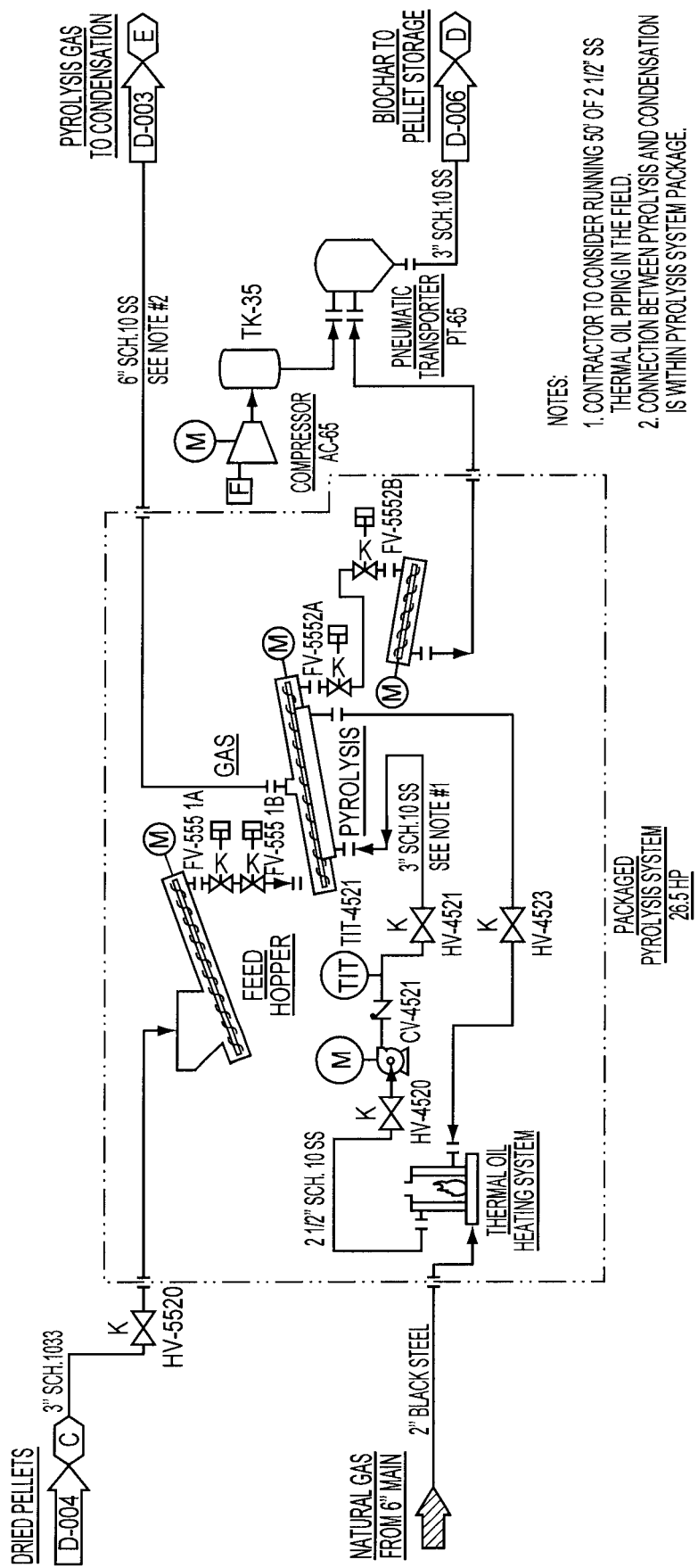
Figure 7:
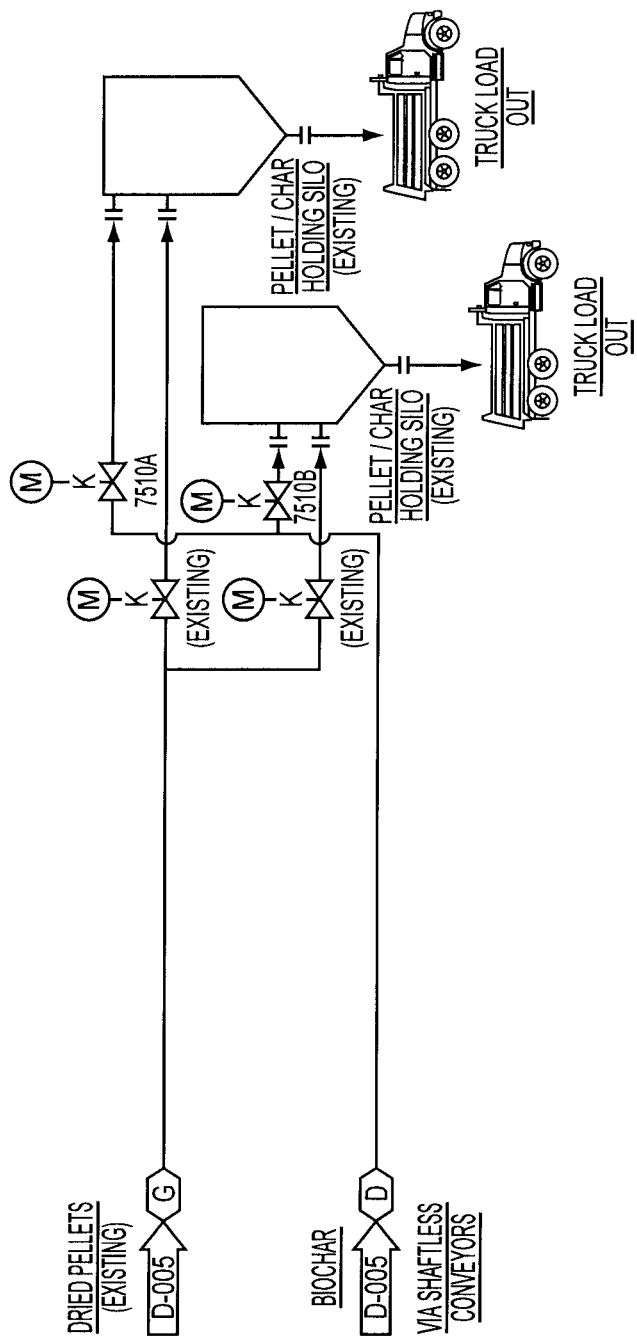
Figure 8:
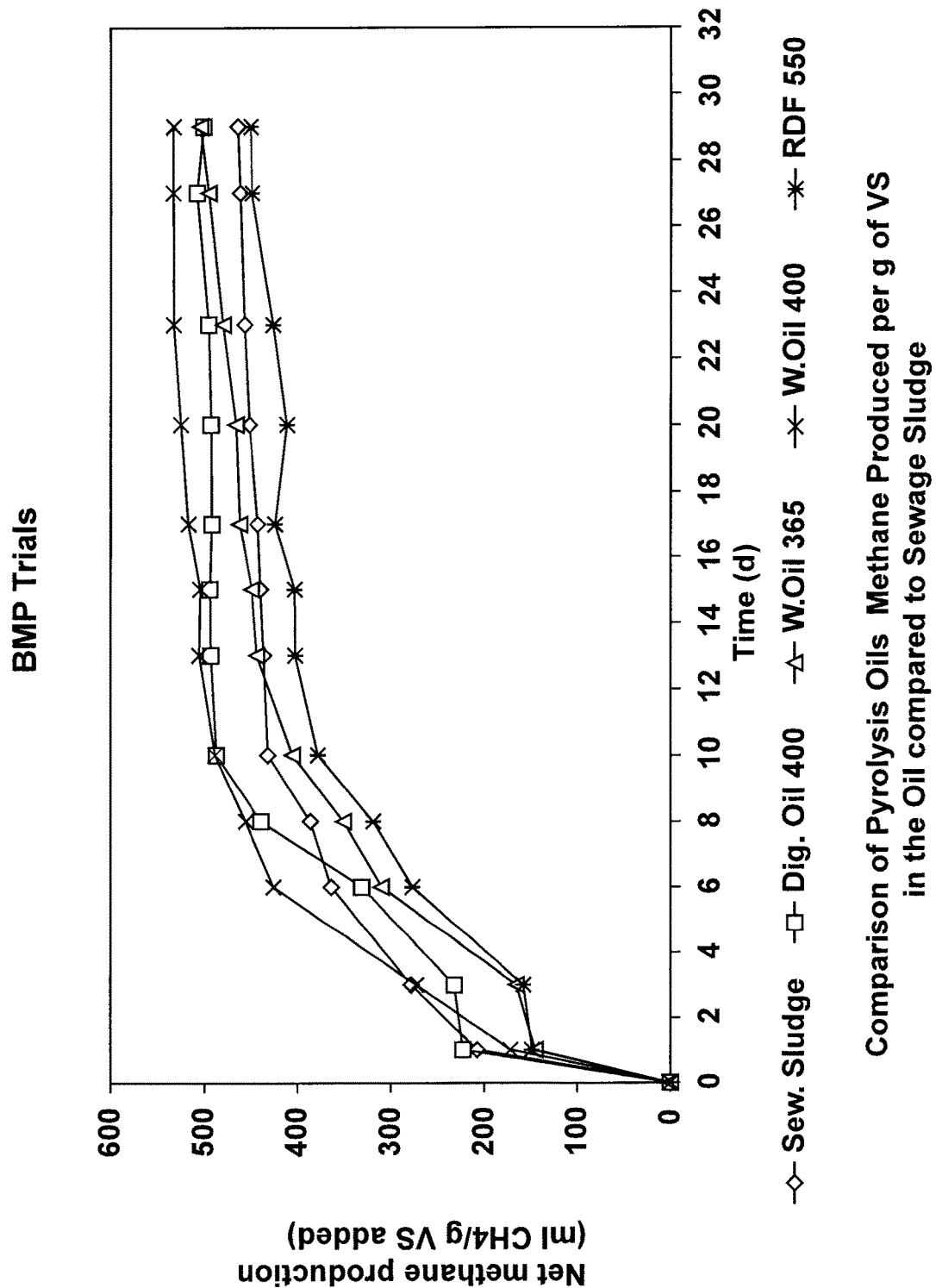
Figure 9:
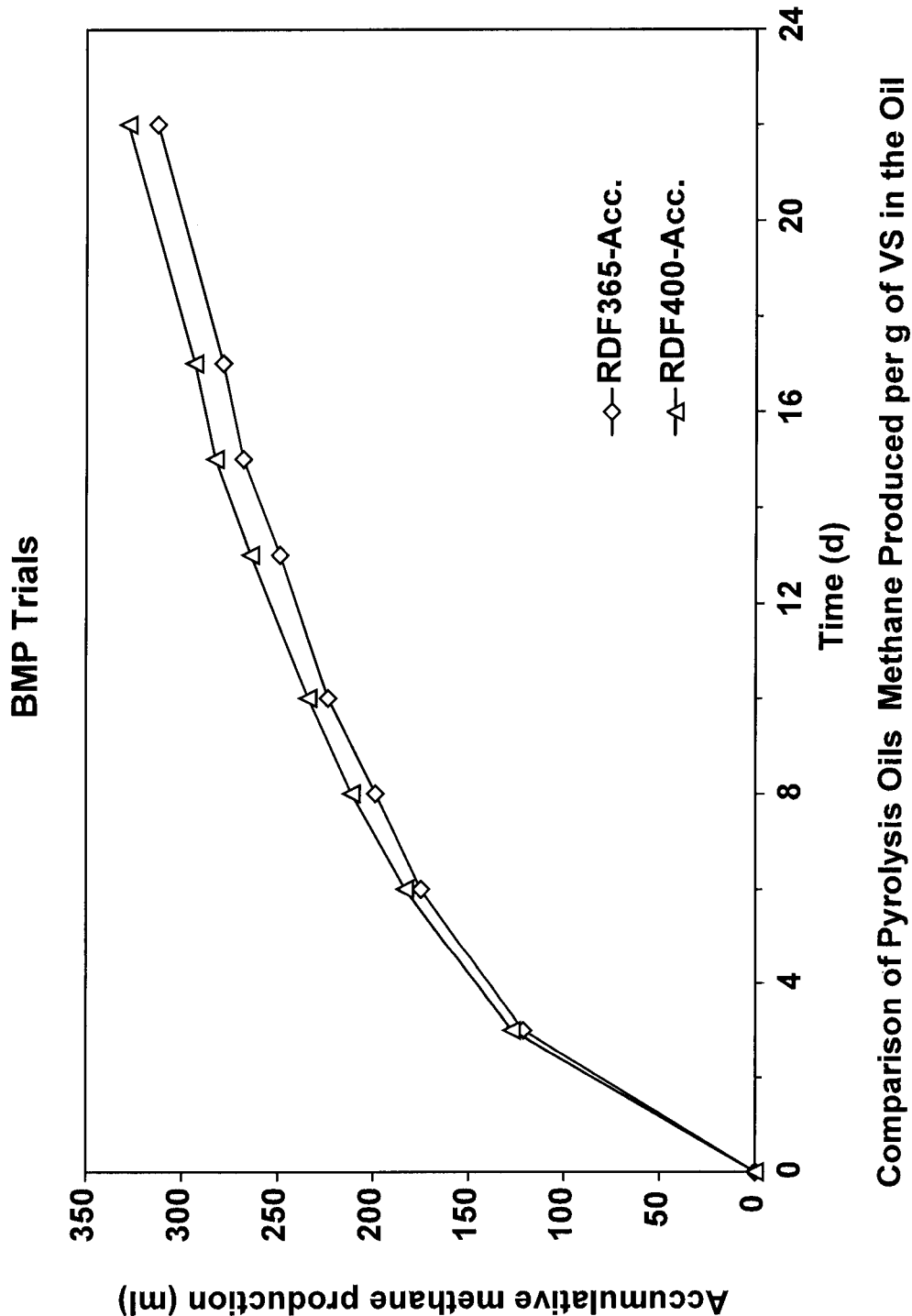
Figure 11:
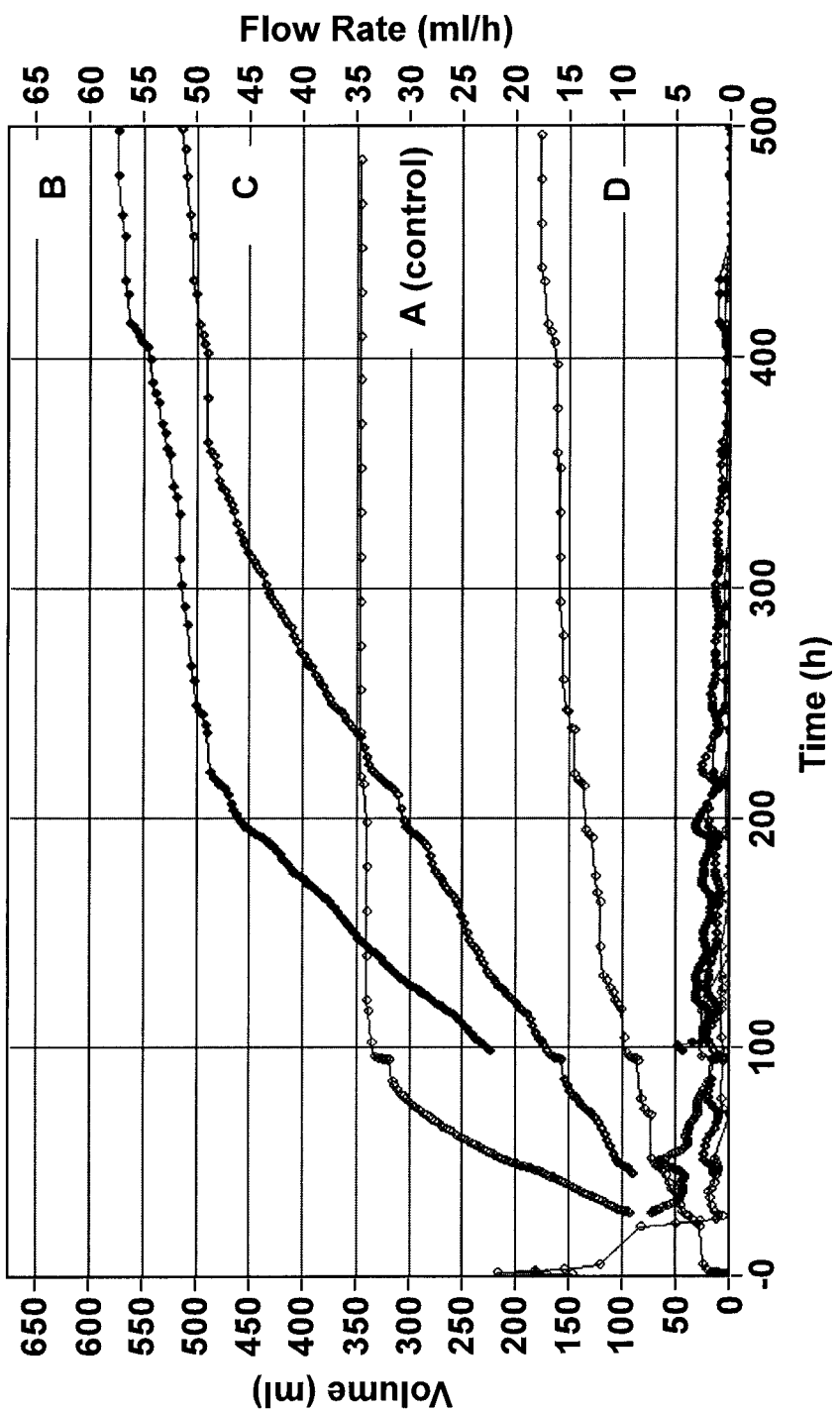
Figure 12:
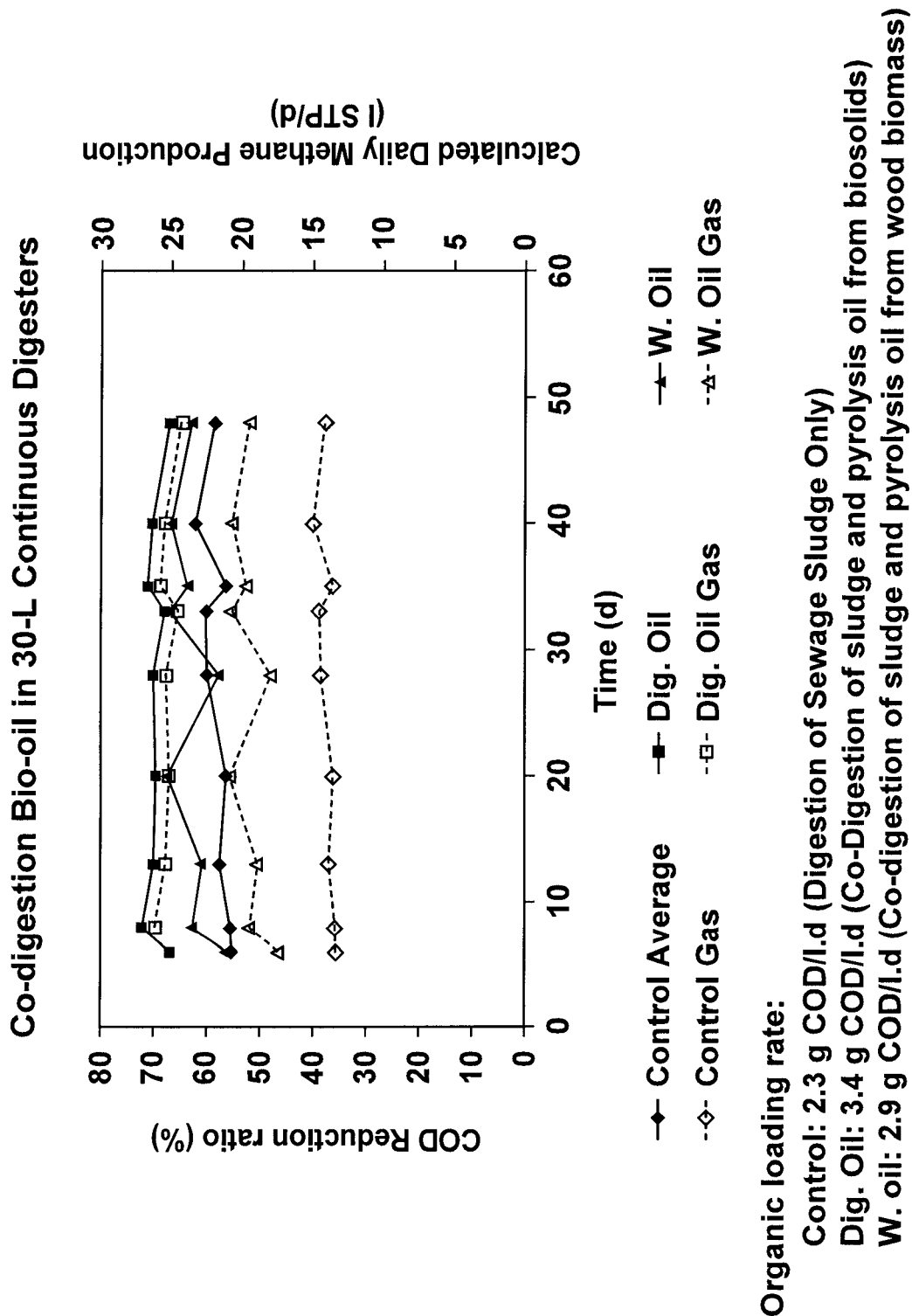

In this specification, the term pyrolysis includes pyrolysis and gasification. The word digestate is sometimes used to refer to only the solids fraction of the sludge produced by an anaerobic digester but in this specification digestate typically refers to the whole digester sludge.

There is experimental evidence that syngas can be converted through anaerobic digestion to biogas containing mainly methane. CO in the syngas is used as a substrate or food for certain strains of methanogenic archea in direct reactions that include hydrogen and water to produce methane. Other indirect reactions also occur, wherein CO and $H_2$ are converted to acetate or methanol and finally to methane by anaerobic bacteria. Regardless of the specific reaction, the methane yield is 0.25 mol of $CH_4$ per mol of CO, plus 0.25 mol of $CH_4$ per mol of $H_2$. Based on the range of CO and $H_2$ typically contained in syngas, this is equivalent to about 0.2 to 0.4 standard $m^3$ of methane production per kilogram of VS gasified, when the syngas is efficiently introduced and dissolved in the anaerobic mixed liquor. The range in syngas composition is a function of the type of biomass gasified and the conditions of the pyrolysis process.

The solids in dewatered digestate cake have a lower energy content than the undigested raw solids in the digester feedstock because a portion of the carbon contained in the VS was converted by digester anaerobic bacteria into methane and carbon dioxide. In the case where a combination of primary and secondary municipal sewage sludge (for example from an activated sludge sewage plant) is fed to a digester, the energy content of undigested solids with a 70% VS content may be about 7000 Btu per pound of dry solids (DS). In anaerobic digester sludge with a 48% VS content, the energy value may be 4800 Btu/lb DS depending on the degree of VS reduction. Depending on the VS content of the raw municipal sewage sludge, its heat content can be as high as 7400 Btu/lb DS, and the heat content of the anaerobic digester sludge may be as high as 5700 Btu/lb DS. The digestate produced from feedstocks with higher fiber content tends to have a higher heat value.

The energy value of the digestate solids can be extracted by pyrolysis or oxidation of the dewatered cake. Depending on the heat content of the digestate solids, further thermal drying after mechanical dewatering may be required to be able to support auto-thermal pyrolysis of the digestate to produce syngas without the need to introduce additional external heat to support pyrolysis. The solids content required to support auto-thermal pyrolysis may range from 40% to 70% or higher. Depending on the type of pyrolysis equipment, required solids content of the feed may be as high as 90%.

The cake can be dried using direct or indirect dryers. Direct belt dryers are more versatile as they enable the use of low temperature heat sources such as heat recovered from engine generators, condensate, etc.

The syngas is introduced into a digester for the purpose of producing methane. The syngas can come from one or more of any form of gasified raw biomass such as wood, municipal solids waste, municipal yard waste (for example grass clippings, leaves or plant clippings), primary or waste activated sludge from a wastewater treatment plant such as a municipal sewage plant, agricultural residues, etc.; or from pyrolysis/gasification of dewatered and partially dried digestate cake produced by the same or other digester at the same or other digestion facility. The facility can be a municipal wastewater treatment plant or an agricultural or industrial digester. Methane production in the digester increases as it results from two sources, the fermentation of VS in the feedstock and the bioconversion of the syngas (CO and $H_2$) to methane. Syngas does not require pretreatment for introduction into the digester, only lowering its temperature. In cases where the pyrolysis feedstock includes lignocellulosic material, pyrolysis allows carbon in the lignocellulosic material to be consumed in the digester.

The solubility of CO and $H_2$ in water is low, therefore syngas biological conversion to methane is limited by the gas-liquid mass transfer. To increase the gas liquid mass transfer rate, the syngas is preferably added to the digestate in small bubbles, for example of 1000 microns or less in diameter, or by transfer across a gas permeable membrane.

A jet ejector pump or aspirator may be used to aspirate syngas. The syngas may be cooled and stored in a gas holder. A pump recirculates sludge from the digester. This pump can be, for example, a chopper pump or an open impeller end suction centrifugal pump. The pump generates a primary flow. An ejector nozzle at the pump discharge reduces the pipe diameter and accelerates the sludge flow, lowering the pressure. This results in a secondary flow of syngas from the gas holder being drawn into the ejector. The turbulence in the ejector nozzle causes an active mixing zone where the liquid and gas are combined into a liquid jet containing fine syngas bubbles. The mixture exits in one or more locations around the lower third of the digester tank where jet nozzles are placed. This increases the mass transfer between gas and liquid and enables the syngas to dissolve in the digestate.

An alternative method to create syngas microbubbles is to use a microbubble generator pump, such as made by Honda Pumps. These pumps are used for dissolved air flotation or ozone injection and create gas microbubbles of 50 micron diameter or less, which may be an order of magnitude smaller than bubbles produced by many gas eductors or aspirators. The microbubbles are dispersed in recirculating digestate or filtrate flow by connecting the pump gas inlet to the syngas storage holder. With smaller bubbles, the gas/water interface surface area is increased, gas holdup time in the water column also increases, and digester foaming is reduced.

The syngas may include one or more condensable gasses. In that cases, the condensable gasses may be introduced into the digester as a gas as described above. Alternatively, at least some of the condensable gas may be condensed and introduced into the digester as a liquid. For example, the syngas may go through an indirect condensing step before remaining gas is fed to the digester.

In digesters with high solids content and fibers in the digestate, a screw press or other solids separator can be used to produce a filtrate that is more suitable for receiving syngas bubbles. The recirculating digestate or filtrate stream is used primarily for gas/liquid mass transfer but may also serve the purpose of total or partial mixing, particularly in digesters operated with low solids content (2 to 4%). In digesters with higher solids content further mechanical mixing is likely to be required. However, mixing may bring syngas bubbles to the surface of the digester before they have a chance to dissolve into the digestate. Many digesters are mixed intermittently, for example ¼ to ⅓ of the time. Optionally, microbubbles or larger ejector or aspirator gas bubbles may be fed only during non-mixing periods to reduce short-circuiting of bubbles to the surface aided by vertical mechanical mixing energy.

When implemented in a high solids digester such as a two stage Triton™ digester from UTS or Anaergia, sludge from the second stage may be used for recirculation and gas entrainment, as the solids content is lower and so is the viscosity. Syngas reintroduction is preferably done in the second stage of high solids two stage digesters. The syngas injection process can be used with mesophilic or thermophilic digesters, but the conversion efficiency of syngas to methane is higher under thermophilic conditions.

An intake to the aspirator nozzle can also be connected to the headspace of the digester, such that the nozzle aspirates a combination of biogas and syngas. The relative flow of the gasses is regulated with valves in one or both gas supply lines. If the quality of the biogas collected in the headspace of the digester decreases (increased CO and $H_2$ content) materially as a result off syngas introduction into the digester liquid, this is an indication of incomplete syngas conversion to methane. Biogas from the headspace can be reintroduced into the digester liquid so that CO and $H_2$ in the headspace gas are converted to methane.

Syngas will exit the pyrolysis reactor at 300 to 550 degrees C., or 400 or 500 to 700 deg C. or more. The syngas is cooled for introduction into the digester. A gas/liquid heat exchanger can be used to recover heat from the syngas. The heat recovered as hot water can be used for partial drying of the cake in a low temperature direct belt dryer. Another option to recover heat from the syngas for cake drying is to use a gas/gas heat exchanger wherein syngas heat is transferred to air used in the belt dryer.

Preferably, the temperature and residence time of the pyrolysis reactor are sufficient to produce syngas wherein components other than water vapor are primarily carbon monoxide or hydrogen. However, there may also be other condensable gasses or liquid droplets in the syngas of other compounds such as oils, waxes or other organics, collectively called "oils" or "organics". A syngas condenser, downstream of or integrated with the gas heat exchanger, condenses the syngas to allow the water vapor and oils to be removed as a liquid fraction of the syngas from a gas fraction of the syngas. The syngas condenser may be, for example, a direct condenser having a recirculated cooled syngas liquid fraction within a contact chamber or an indirect condenser.

The gas fraction of the syngas flows to a gas holder and eventually to the anaerobic digester. The liquid fraction of the syngas optionally flows to an oil-water separator, for example a centrifuge, to create a water fraction and an organics fraction. The water fraction may be discharged for further treatment, optionally to the anaerobic digester if discharge to a sewer is not permitted and no other treatment means are located nearby. The water fraction contains some residual organics and so operates as a bleed preventing the accumulation of recalcitrant compounds.

The organics fraction of the liquid fraction of the syngas may be sent to the digester but it is preferably returned to the pyrolysis reactor. In the pyrolysis reactor, at least a portion of the returned organics are converted to carbon monoxide and hydrogen or other gaseous components of the syngas. This effectively increases the residence time for compounds requiring additional time to be converted into gasses.

Digested sludge disposal in municipal wastewater treatment plants is a growing concern due to rising costs and limitations in the ability to apply the sludge to land. The pyrolysis process results in syngas and char. Char, also called bio-char, contains carbon and ash. Ash is the non-volatile or inert, solids present in the sludge. Some of these solids are nutrients such as phosphorous and potassium or other minerals. Char is a sanitized product as a result of the high temperature process that produces it. The char volume is a fraction of that of the sludge cake, and can be used as soil enhancer. Biochar can be used for one or more purposes such as a soil amendment to improve crop yield, to support crops that require high potash and elevated pH, to improve water quality, to reduce soil emissions of greenhouse gases, to reduce nutrient leaching, to reduce soil acidity, and to reduce irrigation and fertilizer requirements. These positive qualities are dependent on the properties of the biochar, and may depend on regional conditions including soil type, soil conditions, temperature, and humidity. In some cases, modest additions of biochar to soil may reduce nitrous oxide ($N_2O$) emissions by up to 80% and essentially eliminate methane emissions. $N_2O$ and methane are both more potent greenhouse gases than $CO_2$. Biochar can store greenhouse gases in the ground thus potentially helping to reduce or stall the growth in atmospheric greenhouse gas levels. Biochar can sequester carbon in the soil for hundreds to thousands of years, like coal.

In one application, a municipal wastewater treatment plant or process such as an activated sludge plant is coupled with an anaerobic digester. Primary and waste activated (secondary) sludge from the wastewater treatment plant is sent to the digester. The digester produces digestate which is de-watered to produce a cake. The digester sludge cake is further thermally dried and then fed to a pyrolysis system to produce syngas and char. The syngas is cooled, preferably while recovering its heat for example for cake drying. The cooled syngas is introduced into one or more digesters, for example the digester that produced the digestate, for bio-conversion of syngas CO and $H_2$ into methane, mediated by bacteria and archea present in the digester bacterial consortium that also ferments the volatile solids fed to the digester in the raw primary and secondary sludge. Optionally, primary and secondary sludge may be fed first to the pyrolysis system rather than being fed to the digester directly. The methane produced by the two processes in the digester combine in the digester headspace and may be used for energy generation with engines, turbines or fuel cells, or upgraded to biomethane for injection into the natural gas grid. The biochar resulting from the pyrolysis process may be used as soil enhancer. Compared to a system in which a digester merely treated sludge from the wastewater treatment plant, there may be less waste produced or the net energy consumption may be reduced, or both, per unit of sewage treated.

Bio-char from gasification of digested municipal sludge or a digestate from an agricultural or industrial digesters can be used as a soil enhancer or a source of nutrients, mainly phosphorous and potassium.

In an example shown in FIG. 1, an anaerobic digester 1, alternatively referred to as a digester for brevity, is combined with a system for pyrolysing its digestate B. The digester 1 is fed with a feedstock A which may comprise one or more of: a sludge, for example primary or waste activated sludge or both from a wastewater treatment plant such as a municipal sewage plant; municipal solid waste; municipal yard waste; an industrial waste; or, an agricultural waste. The digester 1 produces product biogas O which may, for example, be used to produce energy or upgraded to produce biomethane.

The digester 1 may have one or more mixed covered tanks. Suitable digesters are sold under the Triton™ and Helios™ trade marks by UTS or Anaergia. Digestate B flows from the digester 1 to a mechanical dewatering unit 3, for example a centrifuge, filter press or screw press. The mechanical dewatering unit 3 separates the digestate B into a liquid fraction F and a de-watered digestate cake E. The liquid portion F of the digestate B, in some cases called a filtrate or centrate, may be discharged or re-used, optionally after further treatment. Optionally, the digester 1 may be located near a municipal sewage treatment plant and the liquid portion F may be returned to the municipal sewage treatment plant for further treatment. In this case, the digester preferably treats primary and waste activated (secondary) sludge from the sewage treatment plant either as some or all of the digester feedstock A or as some or all of an optional external biomass for gasification M.

The de-watered digestate cake E is sent to an optional sludge cake dryer 4 if required, or beneficial, to reduce the water content of the cake E before pyrolysis. Hot air and moisture H produced by the dryer 4 may be sent to a heat recovery treatment unit to extract waste heat for reuse, for example to help heat the digester 1, the pyrolysis reactor 5 or the dryer 4. The hot air and moisture H may also be treated, for example to reduce odors, before it is discharged.

The sludge cake dryer 4 produces a partially dried cake G. Some or all of the partially dried cake G which is sent to a pyrolysis reactor 5. Optionally, the pyrolysis reactor 5 may be fed with external biomass M for pyrolysis. The external biomass M may be any one or more of the materials described for the digester feedstock 1. However, the external biomass M is treated by pyrolysis before it enters the digester 1.

The pyrolysis reactor heats its one or more feed materials, for example to between 300 and 550 degrees C., or between 500 and 700 degrees C., in the absence or a deficiency of oxygen, to produce biochar J and hot syngas I. Optionally, biochar J may be used as a soil enhancer typically after being collected and stored temporarily and then hauled off site. Hot syngas I is preferably sent to a gas heat exchanger 6 to produce a cooled syngas K and recovered heat L. Recovered heat L may be re-used in the system or elsewhere. For example, recovered heat L may be used to help heat the digester 1, the pyrolysis reactor 5 or the sludge dryer 4.

Cooled syngas K is optionally sent to a syngas condenser 8. The syngas condenser 8 separates the cooled syngas K into a gas fraction P and a liquid fraction Q. The syngas condenser 8 does not necessarily condense all condensable gasses in the cooled syngas K. The liquid fraction Q may be sent to the digester 1. However, the liquid fraction Q is preferably sent to an oil-water separator 9 to produce a water fraction R and an organic fraction S. The water fraction R may contain some organic compounds and may be treated further before it is discharged or used. The organic fraction S may include water but contains a higher concentration of organic compounds than the liquid fraction Q. The organic fraction S may be treated or upgraded to produce usable products. Alternatively, the organic fraction S is returned to the pyrolysis reactor 5. In this alternative, in the absence of a practical or economical way to make a higher value use of the organic fraction S, the amount of gas fraction P sent to the digester 1 can be increased, which is typically preferable to sending the organic fraction S, or condensable or condensed gases, to the digester 1.

Optionally, the gas fraction P may be collected and stored in a gas holder 7. The gas fraction P may also optionally be mixed with digester biogas N. With or without digester biogas N, the gas fraction P is sent to a pumped gas aspirator 2. Optionally, the gas aspirator 2 may be replaced by another microbubble generator or a gas transfer membrane. recirculating digestate C is withdrawn from the digester 1, typically by way of a pump, and passes through the aspirator 2. Digestate with blended syngas D returns to the digester 1. In this way, the gas fraction P is added to digestate in the digester 1.

Other alternative systems and methods may be devised within the scope of the following claims.

The components and streams in FIG. 1 are listed below, in some cases with additional description.

1. Anaerobic digester
2. Pumped gas aspirator
3. Mechanical dewatering unit
4. Sludge cake dryer
5. Pyrolysis reactor
6. Gas heat exchanger 7. Gas holder (for cooled syngas)
8. Syngas condenser
9. Oil-water separator
A. Digester feedstock
B. Digestate (to dewatering)
C. Recirculating digestate
D. Digestate with blended syngas
E. Dewatered digestate cake
F. Liquid portion (ie. filtrate or centrate) from dewatering, optionally sent to plant headworks or further treatment
G. Partially dried cake (to pyrolysis reactor)
H. Hot air and moisture from dryer, optionally to heat recovery or treatment or both
I. Hot syngas
J. Biochar, optionally to storage or hauling for use as soil enhancer
K. Cooled syngas
L. Recovered heat (from syngas, optionally to cake dryer)
M. External biomass (for pyrolysis)
N. Digester biogas, returning for injection into digester liquid
O. Product biogas, optionally to utilization for energy production or upgrading to biomethane
P. Gas fraction (of syngas)
Q. Liquid fraction (of syngas)
R. Water fraction (of liquid fraction of syngas)
S. Organic fraction (of liquid fraction of syngas)

Design Example

The components and streams in FIG. 1 are listed below, in some cases with additional description.

In North America, Municipal Wastewater Treatment Plants (WWTP's) account for 0.5-0.6% of the entire electricity demand. Additionally, WWTP's can expect to pay an average of $75 per wet ton charge to dispose of generated biosolids. Also, the handling of biosolids produces high amounts of emissions from not only the transport, but from final disposition options such as landfilling, incineration, composting and to a lesser extent land application. In many Municipal WWTP's, sewage sludge is treated in anaerobic digestion facilities, where the volatile solids (VS) fraction of the total solids (typically accounting for 70-80% of the solids) is reduced by 50-55% and the remaining solids is stabilized. The carbon in the VS which is reduced is converted to biogas. Plants who utilize biogas generation for positive use can install Combined Heat and Power (CHP) facilities in order to convert biogas into electricity and heat.

The cost associated with the remaining digested solids is directly related to the mass of the digested solids to be handled. As such, proactive facilities will implement mass reduction processes to dewater the digested solids to a higher solids content cake, typically around 25% TS. This is primarily done either through mechanical pressing or centrifuge. The mass of the digested solids cake, referred to as biosolids, however, can still be further reduced, through drying processes, which evaporates the liquid content, bring the TS to ~90%. WWTP's which implement biosolids drying can see the benefits of reducing their disposal costs by 3.5 times, as well as reducing the greenhouse gas emissions which are emitted from transport vehicles. Still more can be done.

After operations staff, the mentioned energy requirements and biosolids disposal costs are the two highest operational costs for WWTP's. As such, a technology which would improve plant operations in both areas would be attractive to plant operators and reduce the burden on the immediate community. The proposed pyrolysis technology (called "PBM") does just this. PBM further reduces the mass of biosolids to be handled by a WWTP, as well as increases the biogas generated by utilizing the by-products of the biosolids mass reduction process. As part of the PBM process, dried biosolids are treated with the thermal treatment of pyrolysis (in the absence, which includes the near absence, of oxygen). This treatment technology reduces the mass of biosolids by up to 50%, leaving a bio-char product that continues to hold the nutrients present in the biosolids, however eliminating odors and has increased stability.

The pyrolysis technology brings the biosolids temperature up to about 570 deg F. indirectly in the absence of oxygen. In addition to the mass reduction, and conversion of biosolids into bio-char, volatile matter is released from the biosolids during pyrolysis in gas (including vapors) form. The produced gas can be condensed through either direct or indirect means, and as a result two streams are formed as condensate and non-condensables in gas form. The pyrolysis of the biosolids unlocks carbon, breaking down complex carbon chains into simpler forms, which was originally un-digestible when originally treated anaerobically. The unlocked carbon resides in the condensate and the non-condensable gas, and is ideal to be returned to anaerobic digestion to be digested by the anaerobic bacteria and produce biogas. Returning these unlocked energy streams to anaerobic digestion to be treated through the process again can increase biogas production by 30% or more, when co-digested with sewage sludge.

The PBM technology represents an elegant and simple solution whereby WWTP's can become more energy self-sufficient, utilizing an existing renewable energy source in its own biosolids. Furthermore, the technology becomes even more attractive to plant owners and operators due to the cost avoidance associated with the reduced mass of biosolids, having gone through the pyrolysis process. Lastly, all of the nutrient value of the biosolids is retained as solids in the resultant bio-char, only more concentrated, stabilized and odorless. As such, the bio-char product represents a potential value product for WWTP's to be able to potentially gain revenue from its sale as a fertilizer product.

In a design example, a WWTP has a rated capacity of about 45 MGD, and currently has anaerobic digestion facilities to handle all of the plants' sewage sludge. All of the biogas generated at the WWTP is capable of being utilized within the plants' CHP facilities and is currently generating on average 1.4 MW of electricity. or about 75% of the plant electricity demand. Furthermore, the plant employs both digested sludge dewatering and subsequent biosolids drying resulting in 6,300 tons of a 92% TS biosolids pellet.

The proposed project would include installing a biosolids pyrolysis unit within the existing building infrastructure at the WWTP, capable of handling 1 ton/hr of dried biosolids feed. The pyrolysis unit will be operated to match to the plants' drying process regiment, and be able to handle the full amount of dried biosolids. The gas which is generated from the pyrolysis process will be fully captured and passed through a direct condenser unit. The resultant condensate as well as incondensable gas will both be sent to one of the existing plant anaerobic digesters to be co-digested with plant sewage sludge. In addition to the pyrolysis unit the following equipment will be installed as part of this demonstration:

Direct Condensing Unit and recirculating concentrating system
Pyrolysis Thermal Oil Heating System
Pneumatic Transporter for Bio-Char
Condensate and incondensable gas transfer pump and blower system
Piping Connections from Pyrolysis system to Drying and Digestion Facilities
Control Panel and operating system.

Figure 14:
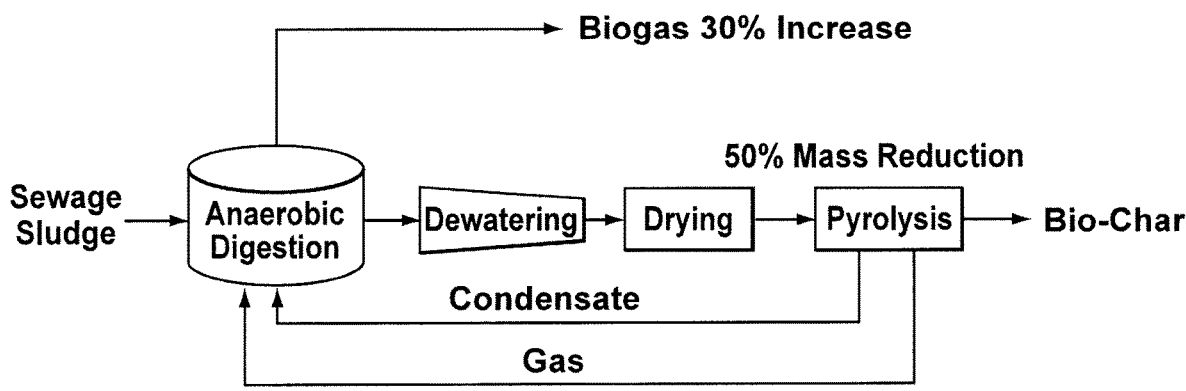
FIG. 14 is a simplified process flow diagram of a pyro-biomethane installation.

A simplified process flow diagram of the PBM installation is shown in FIG. 14. The WWTP will install pyrolysis equipment within the existing building infrastructure, adjacent to the drying facility. For the digestion portion, a digester will be dedicated to the co-digestion of sewage sludge with the pyrolysis by-products of condensate and gas.

The focus of this project is to demonstrate that WWTP's can utilize existing infrastructure and without receiving additional waste streams, be able to increase energy generation, reducing electricity demand from external sources, and optimally become self-sufficient. Specifically, the PDM demonstration project goals and objectives are to achieve one or more of the following: increase the biogas production rate by 30%, where when utilized in the plant's existing CHP facilities can produce on average 1,900 kW of electricity, with the parasitic load of the pyrolyzer equipment included, increase the self-generation capability of the WWTP to 90%, utilize only existing plant dried biosolids as the source for pyrolyzing and subsequent generation of additional biogas, demonstrating the ability to produce renewable energy from an existing renewable fuel source, reduce the mass of dried biosolids for subsequent handling by 45%, retain all nutrient value of the dried biosolids in the resultant bio-char, reduce hauling fees associated with disposing or handling of the dried biosolids, reduce GHG emission reductions associated with biosolids handling.

PFD and P&ID drawings for the proposed changes to the WWTP are shown in FIGS. 2 to 7. Further discussion is provided below.

The treatment of wastewater comprises handling of two major constituents, the liquid fraction and the solids fraction. In typical wastewater treatment, solids are separated from liquid by various means, including mechanically, chemically and biologically. Separated solids in most cases are subsequently treated in Anaerobic digesters where the mass of solids is reduced by micro-biological organisms (biomass) which live in the anaerobic environment and feed on the solids fed to the digester. The purpose of the solids treatment step is to reduce solids mass for disposal, stabilize the solids and produce biogas to generate power for plant use. The bacterial biomass consume a portion of the volatile solids (VS) fraction of the feed to the digester, which typically makes up to 80% of the total solids (TS), and as a by-product of this digestion process, biogas is produced. In typical Mesophilic Anaerobic Digesters, a VS reduction of 50-55% can be expected. The carbon in the VS is converted to biogas. The net result is reducing the total solids handled by the plant by 40-45% and stabilizing the remaining solids. In the process, gas is generated that can be used to produce power. The remaining digested solids are subjected to further processing steps often employed in WWTP's to dewater digested sludge to a higher solids content cake (~25% TS) reducing the mass, typically by mechanically pressing or by centrifuge. The dewatered sludge cake is further handled or disposed of by means such as landfilling, incineration, composting or where possible land application. Regardless of handling method, WWTP operators can expect an average of $75 per wet ton charge to dispose of dewatered digested solids. As such, the disposal of dewatered cake or biosolids is one of the largest contributors to operating costs for WWTP's. Further advancements by WWTP's to implement biosolids drying have been made to further remove water from the biosolids leaving WWTP's such that the solids content is over 90%. Thus, reducing disposal costs by 3.5 times.

Biogas is rich in methane, and when cleaned, can be used as fuel and converted into electricity or pipeline quality renewable natural gas. Across North America, there are 699 WWTP's which utilize anaerobic digestion, with 117 of those plants in California. Cities and municipalities which are looking to further reduce the electricity demand can proactively create their own electricity by burning the generated biogas from Anaerobic Digestion in Combined Heat and Power Units (CHP), and utilize the self-generated electricity within the WWTP. Typically however, the amount of biogas generated by digesting municipal sludge, which utilized in a CHP would only generate about 50% of the parasitic load requirements of an efficiently ran WWTP. That fact combined with large capital costs for CHP installations have seen the amount of WWTP's which install CHP's to be minimal, and as of 2008 in California only 35 MW of CHP capacity was installed at Municipal WWTP's. There are economies of scale however, as the amount of biogas generated from Municipal Sludge is directly proportional to plant flows, but the capital costs of biogas handling and CHP is not directly proportional to capacity. In larger plants over 20 MGD, the payback for installing a CHP can be attractive to plant operators, no so in smaller plants.

The proposed plant modifications are aimed at addressing the two major cost contributors to further reduce the mass of biosolids to be disposed of by a WWTP, as well as increase the biogas generated by utilizing the by-products of the biosolids mass reduction process. The technology is termed "PyroBioMethane" or PBM. Within this technology, dried biosolids are treated with the thermal treatment of Pyrolysis (heated in the absence of oxygen). This treatment technology reduces the mass of biosolids by up to 50%, leaving a Bio-char product that continues to hold the nutrients present in the biosolids, eliminating odors and increases the product stability (does not decompose).

The pyrolysis technology brings the biosolids temperature up to about 570 deg F. indirectly in the absence of oxygen. In addition to the mass reduction, and conversion of biosolids into bio-char, volatile matter is released from the biosolids during pyrolysis in gas form. This Pyrolysis gas is passed through a direct condenser, where the condensables form a pyrolysis condensate that dissolve in the condenser liquid and the non-condensables remain as pyrolysis gas, that also dissolves in the condenser liquid. These products are high in COD and are digestible by anaerobic bacteria. The pyrolysis of digested sludge unlocks carbon that bacteria could not access during the anaerobic digestion process, converts these complex carbon chains into simpler condensables and gas for bacteria to digest and produce biogas. The intention of the PBM technology is to return the condensate and non-condensable gas constituents back to anaerobic digesters, to be co-digested with sewage sludge. By returning the pyrolysis gas and liquid to plant digesters, the digester loading rate is increased, however, does not impact the rate of digestion of sewage sludge. In addition, the returned pyrolysis oil and gas produced in these conditions are easy to digest, enhancing the biogas production by 30% or potentially more.

A PBM demonstration project is proposed at a WWTP with a rated capacity of 45 MGD, and currently has anaerobic digestion facilities to handle all of the plants' sewage sludge. All of the biogas generated at the plant is capable of being utilized within the plants' CHP facilities and is currently generating on average 1.4 MW of electricity. Energy generation, along with efforts to reduce plant parasitic electricity loads allow for the plant to self-generate about 77% of the plant electricity demand. Furthermore, the plant employs both digested sludge dewatering and subsequent biosolids drying resulting in a 92% TS biosolids pellet. The plant produces 6,300 tons of biosolids pellets a year.

The proposed PBM demonstration project would include installing a biosolids pyrolysis unit within the existing building infrastructure at the WWTP, capable of handling 1 ton/hr of dried biosolids feed. The pyrolysis unit will be operated to match to the plants' drying process regiment, and be able to handle the full amount of dried biosolids. The gas which is generated from the pyrolysis process will be fully captured and passed through a direct condenser unit. The resultant condensate as well as incondensable gas will both be sent to an existing plant anaerobic digester to be co-digested with plant sewage sludge. In addition to the pyrolysis unit the following equipment will be installed as part of this demonstration:

Direct Condensing Unit and recirculating concentrating system
Pyrolysis Thermal Oil Heating System
Pneumatic Transporter for Bio-Char
Condensate and incondensable gas transfer pump and blower system
Piping Connections from Pyrolysis system to Drying and Digestion Facilities
PyroBioMethane Control Panel and operating system.

The plant has incorporated bi-solids drying into their facility, and currently has the ability to dry all biosolids the plant produces. The staff has actively marketed the current biosolids pellets as a fuel source and delivers 70% pellet production to this market. This market receives a very small tipping fee for the product, that does not offset the current transportation costs. As the nutrients in the biosolids are retained in the bio-char product, only now further concentrated, there is an increased potential for that bio-char to be sold as a fertilizer product, at a more substantial premium as it is a more stable, odorless, has more water bearing capacity and is easily transported and stored for blending as a soil amendment.

The PyroBioMethane (PBM) technology has been successfully trialed. Dried municipal biosolids has been pyrolyzed in a batch unit to produce the products of pyrolysis: Bio-char, Pyrolysis Oil and Pyrolysis gas. In a batch pyrolysis unit, pyrolysis gas is passed through an indirect condenser, from which the gas stream is separated into two, the condensables and non-condensables. Following pyrolysis, the condensable portion, or pyrolysis oil was co-digested with sewage sludge in batch digestion tests, where the biogas production was seen to be increased compared to control digesters which were only fed sewage sludge.

Results of some batch trials conducted by CDM consultants were presented in March 2012, at the WEF residuals and biosolids conference (Parry, 2012). In CDM's work, dried biosolids from the Pierce County Chambers Creek Regional WWTP in Washington State were pyrolyzed in a batch pyrolyzer, and the condensate was subsequently co-digested with sewage sludge in a batch digestion trial. In CDM's trials, comparison digesters with identical seed sludges (digested sludge) were fed with in the control case thickened sludge only (1.5 g COD) and in the comparison case thickened sludge+condensate from pyrolysis (1.5 g COD from sludge+1.5 g COD from condensate). Additionally a batch digester, with only seed sludge was observed. The results of the comparison cases are shown in Table #1 below, where the methane produced in the digester with condensate produced 50 ml more methane (350 ml compared to 300 ml). When the comparison values are reduced by the amount of methane produced by the seed sludge (120 ml), the resultant difference represents a 28% increase in methane production, when condensate from pyrolysis is co-digested with sewage sludge.

TABLE #1

CDM Batch PBM Results

| Digester Feed | Methane Produced (mL) |
|---|---|
| Digested Sludge Only (seed) | 120 |
| Digested Sludge + thickened sludge | 300 |
| Digested Sludge + thickened sludge + condensate | 350 |

Further to the CDM trials, the Applicant has conducted batch pyrolysis and subsequent digestion trials similar to CDM. In our studies, dried pellets from the WWTP described above were pyrolyzed at a temperature of 523F, and similarly pyrolysis gas was passed through an indirect condenser and the condensate collected for digestion trials. In our batch digestion trials, comparison digesters were again trialed where the cases are shown in Table #2 below:

TABLE #2

Batch PBM Results

| Digester Feed | Methane Produced (mL) |
|---|---|
| Digested Sludge + raw sewage sludge | 350 |
| Digested Sludge + raw sewage sludge + condensate | 531 |

Figure 15:
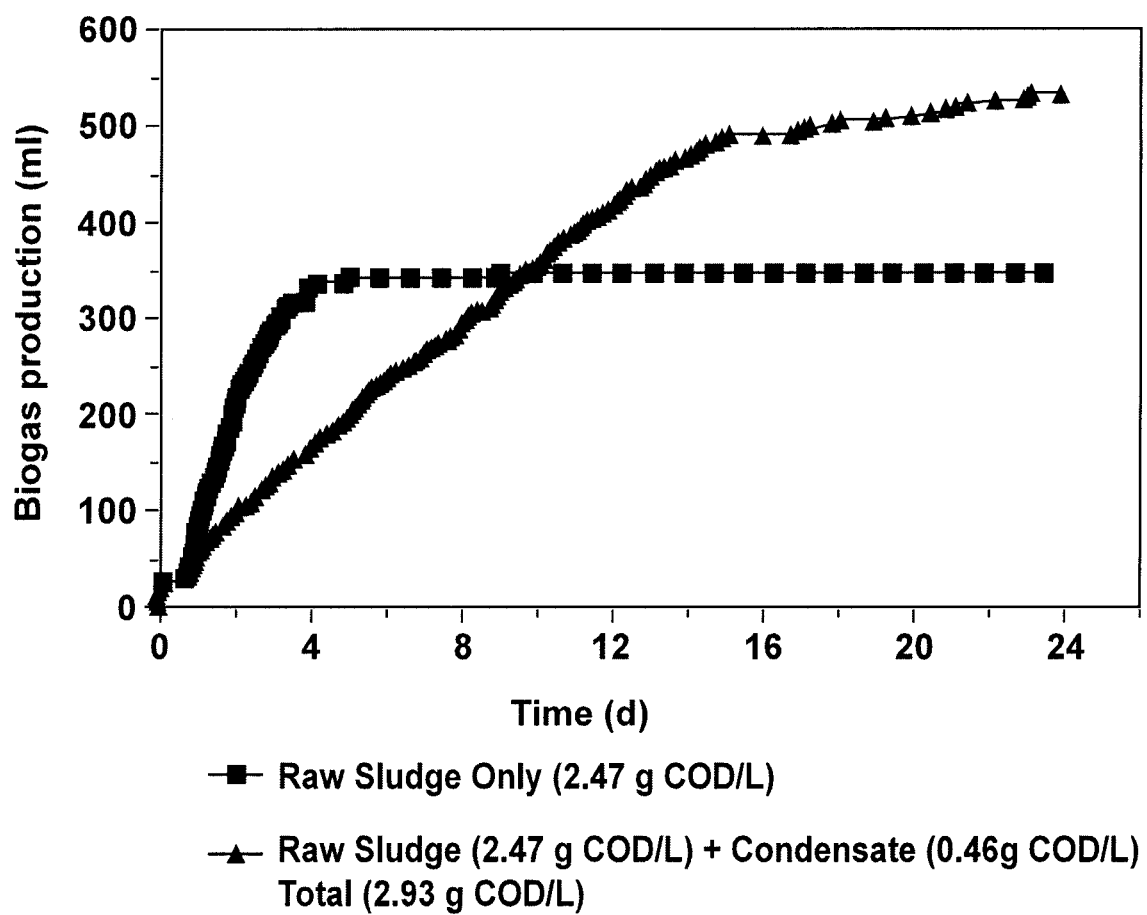
FIG. 15 is a graph of biogas production in a trial.

As can be seen from our trials, the biogas production from the digester where condensate was co-digested with sewage sludge, showed a 51% increase in biogas production. It is noted that the loading rate applied in the co-digested digester in terms of COD loading is representative of a full scale Municipal digester loading where the loading is made up of a typical loading rate contributed by sewage sludge, plus the additional loading associated with the pyrolysis condensate generated by pyrolyzing the same mass rate of digested sludge which would have been seen from the respective sewage sludge loading. A graphical representation of the biogas production in our trials is shown in FIG. 15.

PBM Biogas Production Vs. Control

In the CDM and our trials respectively, the mass reduction of dried biosolids was 46% and 49% respectively. The results from these two studies support our projection that Municipal WWTP biogas production can be increased by 30%, without the need to add external waste streams, simultaneously reducing biosolids mass by greater than 45%.

The largest deterrent for Municipal WWTP's with Anaerobic Digestion facilities to utilize biogas is the capital investment associated with installing Combined Heat and Power (CHP) technology. The capital cost is proportionally high for small to medium sized WWTP's (typically below 10 MGD), with long payback periods. The additional biogas generated from utilizing PBM technology will make the installation of CHP facilities more widespread across WWTP's more attractive because of the increased biogas production. Furthermore, investment recovery for drying and pyrolysis equipment installations is easily seen from cost avoidance on tipping fees for resultant plant biosolids. The technologies within the PBM solution are developed on sound thermal, mechanical, biological and chemical processes, which have been implemented and optimized on their own in countless full scale WWTP's globally.

Although there are 117 WWTP's with Anaerobic Digestion in California, few currently have combined heat and power (CHP) facilities totally a capacity of only 35 MW in 2008, mostly in centralized in a few large plants. The installation of CHP facilities is often prohibitive due to the relative high capital cost associated with the installation of gas handling and CHP facilities, especially in small to medium sized WWTP's, and the payback on the capital investment is not attractive. By including PBM technology, the amount of biogas produced is increased and, thus the CHP size for installation could increase, allowing WWTP's to take advantages of economies of scale, and result in the installation of CHP's to be more widespread supporting the goal of 6,500 MW of additional combined heat and power capacity by 2030.

The PBM technology is a carbon negative process, and sequesters carbon in the resultant bio-char. As per CalRecycle, California generates 750,000 dry tons of biosolids every year. For every ton of sewage sludge landfilled, 1.01 tons of CO2 eq is emitted into the atmosphere, similarly 1.63 tons of CO2 eq when incinerated (Beam, 2009). This value is reduced to 0.22 tons of CO2 eq when composted and further reduced to 0.13 tons of CO2 eq when sludge is land applied (Hobson, 1996). These emissions can be eliminated when sludge is pyrolyzed and converted to bio-char. Currently in California 18% of all sewage sludge is landfilled, 8% incinerated, 16% composted and 54% land applied. Eliminating fractions that are landfilled, incinerated and composted would reduce GHG emissions by 260,550 tons of CO2 eq annually. Accordingly, the process can include a step of calculating and claiming or transferring a greenhouse gas reduction credit.

It has been seen that inhibitory compounds to digestion are released at elevated pyrolysis temperatures, as such tight controls on product temperatures during pyrolysis are preferred.

Other names commonly used to describe pyrolysis are "destructive distillation", "low temperature carbonization" and "torrefaction". Bio-char produced from sewage sludge can be used to enhance agricultural processes. Digester gas can be used to operate internal combustion engines, gas turbines, and fuel cells. As mentioned previously, in California, there are 117 WWTP's which have anaerobic digestion facilities. That number grows to 699 when extended to North America. With the elegance of the PBM technology to provide plants with an attractive payback driven by cost avoidance of the disposal of biosolids, add to it the increase of biogas production, and more WWTP's are going to be pushing to install CHP facilities to utilize the total plant biogas for self-generation. While there was only 35 MW of installed CHP's as of 2009, the successful demonstration of PBM will support the adopting of CHP facilities, thus increasing the self sufficiency of WWTP's.

Further Discussion

Optionally, biogas production could be further increased by also pyrolysing another waste source, such as green waste, municipal solid waste (MSW) or refuse derived fuel (RDF). The products, condensable and non-condensable, may be added to an anaerobic digester. A pyrolyzer treating MSW or RDF may be operated at 300-550 degrees C. MSW and RDF include some items such as plastics that are not effectively pyrolyzed at lower temperatures. While lower temperatures (or at least temperatures at the low end of the range given in this paragraph) increase the digestible portion of biomass pyrolysis products, pyrolysis of biomass at these temperatures does not produce excessive amounts on methanogen inhibitory compounds (as do higher temperatures). Thus the temperature range of 300-550 degrees C. is suitable for pyrolysing a feed comprising biomass and MSW or RDF. The effect of temperature and feed composition on pyrolysis product digestion is further descried in the experimental results shown in FIGS. 8 to 12.

Pyrolysis of biosolids can be conducted in one or more screw type heat exchanger as described, for example, in U.S. Pat. No. 5,417,492 or US Publication Number 2010/0223839 which are incorporated by record. Whether this type of reactor or another is used, the reactor may have a plurality of zones, each with a temperature and dwell time. An upstream zone may have high barrel temperature (optionally higher than the desired pyrolysis temperature) to bring the feedstock up to a desired pyrolysis temperature and evaporate moisture. The dwell time in this upstream zone is preferably the minimum required to evaporate essentially all of the water in the feedstock while bringing the feedstock up to, but not over, a desired pyrolysis temperature. After water has been removed, pyrolysis of dried biosolids for a 15-25 minutes, preferably 20 minutes, dwell at 300-400 C, preferably 320-350 C, feedstock temperature produces pyrolysis oil optimized for digestion (volatile solids (VS around 50 wt %, over 40 wt % Carbon). Increasing the dwell time optionally increases oil production, but reduces char amounts, while maintaining oil quality for digestion. Increased temperatures can help provide a consistent oil quality and means to decrease dwell times, but limits the type of heating medium. Biomass is best treated at temperatures under 400 C in order to get the readily digestible volatiles, leaving the rest in the char. Pyrolysis of RDF is best done under 400 C to only volatilize cellulosic materials (Woods, paper, etc.) as well as any dried digestate. Above 400 C, pyrolysis of the plastics also occurs. If this is desired, the pyrolysis temperature may be increased to about 550 C while still producing acceptable products for digestion from the biomass.

In order to pyrolyze any feedstock, the product must first be brought up to pyrolysis temperature, and typically excess moisture should be evaporated. These steps increase the product dwell time in the pyrolyzer, the increase in dwell time being inversely related to the temperature of the heat source used to heat the feedstock. Accordingly, it is preferably to operating a pyrolyzer with at least two zones, a drying zone and a pyrolysis zone, operated at different temperatures. The pyrolysis zone has a temperature selected to provide the desired feedstock temperature for pyrolysis. The drying zone has a higher temperature to heat the feedstock rapidly and remove moisture. The dwell time in the drying zone is preferably selected to be the minimum required to bring the feedstock within the pyrolysis temperature range and, optionally, to evaporate a desired amount of water. In this way, the overall dwell time is reduced which allows a smaller pyrolysis unit to be used.

Lower temperatures and/or short dwell times in the pyrolysis zone lead to pyrolysis liquids that are low in volatile solids and carbon, which is undesirable. We have observed that a carbon content of 30 wt % or more is desirable in pyrolysis liquids because this increases the production of biogas. A minimum pyrolysis dwell time appears to be required to produce digestible pyrolysis liquid.

For example, dwell times of 10 minutes or less produce liquids which have a very low carbon content (10 wt % or less) and lead to having poor biogas production when digested. Additionally, pyrolysis with low dwell times will result in a poor conversion to gas. In contrast, dwell times of about 20 minutes have proven to produce a liquid (condensate) which is rich in carbon content (above 40 wt %), and is readily digestible. It is estimated that a dwell time of 15 minutes or more, or 20 minutes or more, at a pyrolysis temperature of 285 degrees C. or more, or 300 degrees C. or more will produce readily digestible pyrolysis liquid.

In one example, dried digestate was pyrolyzed for a 20 minute dwell time at a 320 degrees C. product temperature. The feedstock temperature is assumed to be close to the product temperature. This produced liquids having a volatile solids (VS) concentration of about 50 wt % and a carbon content of over 40 wt %. Increasing the dwell time increases the production of liquids over char while maintaining the quality of the liquids for digestion. Increased temperature can also produce liquids suitable for digestion and may also allow for some decrease in dwell time. However, high temperatures limit the types of heating medium that may be used. Further, when treating biomass, temperatures of over about 400 to 450 degrees C. are unlikely to be efficient since the readily attainable volatiles have already been extracted from the feedstock. Beyond those temperatures, char continues to be converted into other products, but more of the product is produced as non-condensable gas, and pyrolysis energy consumption also increases with temperature. Although non-condensable gas can be digested, it is energy intensive to mix gas with the digester liquid and so it is typically preferable to stay below a temperature in the range of 400 to 450 degrees C. and leave more of the feedstock as char.

At a 20 minute dwell time, a minimum temperature of 285 degrees C. or more appears to be required to produce carbon rich liquid pyrolysis products, ie with carbon contents of 25 or 30 wt % or more. Increased temperatures of over 300 degrees C. and up to 350 degrees C. for dried biosolids continued to produce carbon rich digestible liquids, as indicated by their bio-methane potential (BMP). Tests on various liquid pyrolysis products indicate that BMP can be correlated to the % by mass of carbon content. The presence of inhibitory compounds was not detected in pyrolysis liquids that had been produced at temperatures up to 350 degrees C.

It is expected that shorter dwell times may be acceptable if higher pyrolysis temperatures are used. However, low temperature pyrolyzers may be easier and less expensive to produce. Further, significant dwell times are still required at higher temperatures. For example, in one trial an anaerobic digester was operated for a first period of time without adding pyrolysis products. The digester was fed with sludge from a wastewater treatment plant at a rate of 2.3 g of sludge COD per litre of digestate in the reactor per day (g COD/L*d). In a second period of time, pyrolysis liquid was added at a rate of about 0.2 g COD/L*d. This pyrolysis liquid was produced by pyrolysing waste digestate from the digester at 320 degrees C. with a dwell time of 20 minutes. This liquid had 50 wt % VS and over 40 wt % carbon and caused an increase in biogas production from the digester. In a third period of time, another pyrolysis liquid was added at a rate of about 0.2 g COD/L*d. This pyrolysis liquid was produced by pyrolysing waste digestate from the digester at 365 degrees C. with a dwell time of 10 minutes. This liquid had 42 wt % VS but only about 10 wt % carbon. Adding this pyrolysis liquid caused a decrease in biogas production to below the production in the first period of time. In another time period, a pyrolysis liquid was added at a rate of about 0.4 g COD/L*d. This pyrolysis liquid was produced by pyrolysing waste wood at 325 degrees C. with a dwell time of 10 minutes. This liquid had 51 wt % VS but only about 23 wt % carbon. Adding this pyrolysis liquid caused biogas production to near, but still slightly below, the production in the first period of time. These experiments indicate that the amount of carbon in the liquid pyrolysis products (ie. pyrolysis oil obtained by separating condensable gasses from the gasses and vapors produced) increases with dwell time of the feedstock in the pyrolysis zone of a pyrolyzer. VS concentration also increases with dwell time but to a lesser extent. A minimum carbon content of about 25 or 30 wt % appears to be desirable to make the liquids digestible, or to cause an increase in biogas production. Attaining this carbon concentration requires a dwell time of 15 or 20 minutes or more. In these trials, the pyrolysis liquids are returned to the digester without separating the liquids into different components.

In some cases, digestate is dried and formed into a pellet and sold as a fuel for combustion. Char produced after pyrolysis may similarly be sold as a fuel for combustion. The char is more stable than dried digestate pellets, and gives of less odors and dust. In some cases, subject to meeting requirements regarding contaminant concentration levels, the char may also be sold for use as a soil enhancer. In this case, the char sequesters carbon and may allow a carbon or greenhouse gas credit, offset, or tax benefit to be claimed for the process of transferred to another party.

Cozzani et al., in "A Fundamental Study on Conventional Pyrolysis of a Refuse-Derived Fuel", Ind. Eng. Chem. Res. 1995, 34, 2006-202, considered the behavior of some of the components of RDF under pyrolysis at varying temperatures. Wood and paper components were found to experience nearly all of their weight loss at temperatures up to about 425 (or 400 to 450) degrees C. A polyethylene component, however, experienced almost no weight loss up to about 400 degrees C. but experienced nearly all of its weight loss at temperatures up to about 550 degrees C.

Our experiments indicate that biomass other than wood and paper is also almost entirely converted by pyrolysis at temperatures up to about 400 to 450 degrees C. The weight percentage of plastic in RDF is generally low and plastic is relatively inert. Accordingly, the additional amount of liquid or gas for digestion generated by using a pyrolysis temperature above a temperature of about 400 to 450 degrees C. provides a small return relative to the energy required to heat the RDF to 550 degree C. Further, handling vapors produced by pyrolyzing plastics can be difficult. Accordingly, and since removing plastics provides no additional benefit in making the char stable or odor free, and because the heating value of the plastic remains in the char, it can be preferable to pyrolyze RDF or any other feed stock comprising plastic at a temperature below a temperature in the range of 400 to 450 degrees C., for example at 425 degrees C. or less, particularly when the char will be used as a fuel for combustion.

Cozzani et al. also reported the ratio of non-condensable gas to liquids increased with increasing temperature from 500 degrees C. to 900 degrees C. This generally encourages the use of higher temperatures when gas products are desired. In the present case, although gas products can be sent back to the digester, it is more energy intensive to mix gasses with sludge in the digester than to add liquids to the digester. Accordingly, in the present case it is not desirable use pyrolysis temperatures over 550 degrees C.

In experimental examples, pyrolysing RDF required 1.3 kWh/kg of energy and yielded a product that was 48% char, 44% oil and 8% gas. The density of the char was increased by 132% relative to the original feed. Assuming that the oil and gas are sent to an anaerobic digester, the amount of solid product (char) to be handled further is reduced by 52% in mass and 79% in volume. In another experimental example, pyrolysing green waste required 0.4 kWh/kg of energy and yielded a product that was 44% char, 27% oil and 29% gas. The density of the char was increased by 352% relative to the original feed. Assuming that the oil and gas are sent to an anaerobic digester, the amount of solid product (char) to be handled further is reduced by 56% in mass and 86% in volume. In another experimental example, pyrolysing dried digestate pellets required 0.2 kWh/kg of energy and yielded a product that was 53% char, 34% oil and 13% gas. The density of the char was increased by 34% relative to the original feed. Assuming that the oil and gas are sent to an anaerobic digester, the amount of solid product (char) to be handled further is reduced by 47% in mass and 60% in volume.

Figure 13:
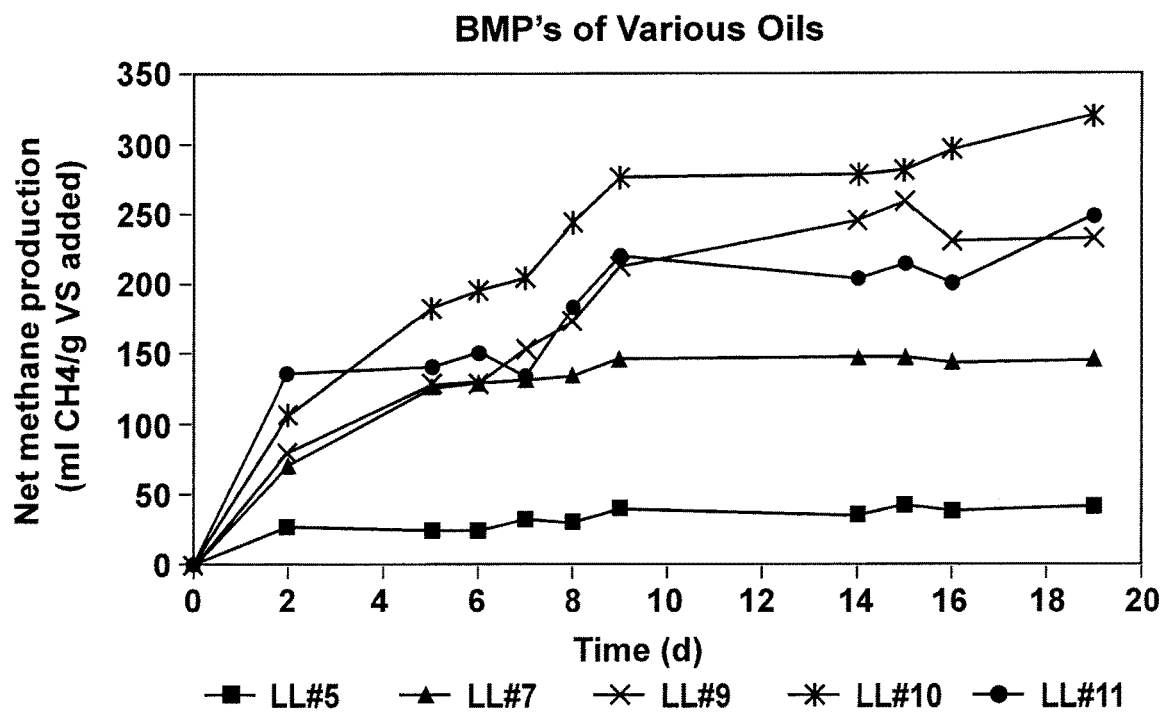
FIG. 13 is another graph of experimental results.

In other experiments, dried digestate pellets were pyrolyzed under conditions shown in Table 3 below. Liquid (oil) produced from these trials had the components shown in Table 4 below. Bio-methane potential (BMP) of liquids from trials 5, 7, 9, 10 and 11 as described in Tables 3 and 4 are show in FIG. 13.

We claim:

1. A process comprising steps of,
   a) producing a gas including condensable vapors and non-condensable gasses from pyrolysis of a feedstock at a temperature of 400° C. or more; and,
   b) adding the gas to an anaerobic digester, wherein the condensable vapors are added in either vapor or liquid form,
   wherein the feedstock comprises biomass and plastic.

2. The process of claim 1 wherein the biomass comprises one or more of a raw biomass, wood, municipal yard waste, municipal solids waste, primary sludge from a wastewater treatment plant, waste activated sludge from a wastewater treatment plant, an agricultural waste or residue, and refuse derived fuel.

3. The process of claim 1 wherein the biomass comprises digestate.

4. The process of claim 1 wherein the biomass comprises digestate and one or more of a raw biomass, wood, municipal yard waste, municipal solids waste, primary sludge from a wastewater treatment plant, waste activated sludge from a wastewater treatment plant, an agricultural waste or residue, and refuse derived fuel.

5. The process of claim 3 wherein the digestate is produced by the anaerobic digester or another anaerobic digester receiving a similar feed or both.

TABLE #3

| Trial No. | Screw Temp. (° C.) | Product Temp. (° C.) | Dwell time (min) | Total pellet (lb.) | Char (%) | Oil (%) | Gas (%) | Energy consumption (kWh/kg pellets) |
|---|---|---|---|---|---|---|---|---|
| 1 | 320 | 215 | 15 | 10 | 90 | 9 | 2 | 0.099 |
| 2 | 320 | 215 | 20 | 10 | 90 | 9 | 2 | 0.140 |
| 3 | 365 | 239 | 15 | 10 | 87 | 11 | 2 | 0.105 |
| 4 | 365 | 239 | 20 | 10 | 81 | 15 | 5 | 0.147 |
| 5 | 365 | 239 | 30 | 10 | 70 | 21 | 9 | 0.264 |
| 6 | 400 | 275 | 10 | 10 | 84 | 13 | 3 | 0.319 |
| 7 | 400 | 275 | 20 | 10 | 66 | 25 | 9 | 0.341 |
| 8 | 425 | 285 | 20 | 10 | 58 | 32 | 11 | 0.374 |
| 9 | 450 | 320 | 20 | 20 | 59 | 31 | 11 | 0.149 |
| 10 | 500 | 320-330 | 20 | 30 | 54 | 33 | 13 | 0.198 |
| 11 | 525 | 340 | 20 | 15 | 50 | 43 | 7 | 0.227 |
| 12 | 500-515 | 315-325 | 20 | 252.6 | 53 | 34 | 13 | 0.233 |

TABLE #4

| Item | #5 Dig Oil 239, DT30 | #7 Dig Oil 275, DT20 | #8 Dig Oil 285, DT20 | #9 Dig Pellet Oil 320, DT20 | #10 Dig Pellet Oil 340 | #11 Dig Oil |
|---|---|---|---|---|---|---|
| C (wt %) | 10.62 | 9.42 | 39.01 | 38.36 | 43.89 | 44.86 |
| H (wt %) | 10.70 | 11.18 | 11.59 | 10.39 | 10.39 | 10.08 |
| D (wt %) | 75.67 | 75.54 | 41.73 | 43.46 | 37.33 | 35.94 |
| N (wt %) | 1.40 | 2.63 | 5.53 | 5.77 | 6.45 | 7.06 |
| S (wt %) | 1.55 | 1.21 | 1.88 | 1.84 | 1.81 | 1.92 |
| Moisture (wt %) | 54.36 | 45.54 | 45.53 | 41.26 | 36.80 | 50.23 |
| TS (wt %) | 45.64 | 54.46 | 54.47 | 58.74 | 63.20 | 49.77 |
| VS (wt %) | 43.72 | 54.24 | 53.46 | 57.36 | 61.57 | 48.69 |
| TS (mg/ml) | 502 | 599 | 599 | 646 | 695 | 547 |
| VS (mg/ml) | 481 | 597 | 588 | 631 | 677 | 536 |
| ThOD (g O2/g TS) | 0.85 | 0.68 | 2.75 | 2.32 | 2.46 | 3.14 |
| ThOD (g O2/g VS) | 0.82 | 0.68 | 2.70 | 2.26 | 2.40 | 3.08 |
| BMP ThOD (ml CH4/g VS removed) | 287 | 236 | 946 | 792 | 840 | 1077 |
| ThOD (g O2/g bio-oil) | 0.39 | 0.37 | 1.50 | 1.36 | 1.56 | 1.57 |
| ThOD (mg O2/ml bio-oil) | 429 | 406 | 1650 | 1498 | 1713 | 1722 |
| $BMP_{TPCS}$ (ml CH4/g bio-oil decomposed) | 137 | 129 | 525 | 477 | 545 | 548 |

6. The process of claim 1 wherein the anaerobic digester is coupled with or part of a municipal wastewater treatment plant, or an agricultural or industrial digester.

7. The process of claim 1 wherein the gas is cooled before it is fed to the digester.

8. The process of claim 1 wherein vapors of condensable organic compounds are removed from the gas and returned as feedstock to step a).

9. The process of claim 1 comprising, before step a), a step of heating the feedstock wherein the heating step comprises contacting the feedstock with a medium at a higher temperature than a heating medium used in step a).

10. The process of claim 1 comprising wherein in step a) the feedstock is pyrolyzed for 15 minutes or more.

11. The process of claim 1 wherein the vapor portion of the gas has a carbon content of 25 wt % or more.

12. The process of claim 1 wherein in step a) the feedstock is pyrolyzed at a temperature of 550 degrees C. or less.

13. The process of claim 1 wherein the vapor portion of the gas has a carbon content of 30 wt % or more.

14. The process of claim 1, wherein adding the gas to an anaerobic digester comprises adding gas to digestate from the anaerobic digester.

15. The process of claim 14, wherein the gas is added to digestate in a recirculating digestate loop.

16. The process of claim 15, further comprising adding a portion of the mixture of gasses from the anaerobic digester to the digestate in the recirculating digestate loop.

* * * * *